US008309766B2

(12) United States Patent
Nebolsin et al.

(10) Patent No.: US 8,309,766 B2
(45) Date of Patent: Nov. 13, 2012

(54) PHENYL-CONTAINING N-ACYL AMINE AND AMINOACID DERIVATIVES, METHODS FOR THE PRODUCTION THEREOF, A PHARMACEUTICAL COMPOSITION AND THE USE THEREOF

(75) Inventors: Vladimir Evgenievich Nebolsin, Moscow (RU); Tatyana Alexandrovna Kromova, Kaluga (RU); Galina Alexandrovna Zheltukhina, Moscow (RU); Violetta Leonidovna Kovaleva, Moscow (RU)

(73) Assignee: Obschestvo S. Organichennoi Otvetstvennostiyu Pharmenterprises, Moscow (RU)

( * ) Notice: Subject to any disclaimer, the term of this patent is extended or adjusted under 35 U.S.C. 154(b) by 978 days.

(21) Appl. No.: 11/886,965

(22) PCT Filed: Mar. 24, 2006

(86) PCT No.: PCT/RU2006/000139
§ 371 (c)(1),
(2), (4) Date: Oct. 23, 2008

(87) PCT Pub. No.: WO2006/101422
PCT Pub. Date: Sep. 28, 2006

(65) Prior Publication Data
US 2009/0111874 A1    Apr. 30, 2009

(30) Foreign Application Priority Data
Mar. 25, 2005 (RU) .............................. 2005108492

(51) Int. Cl.
*C07C 233/05* (2006.01)
*A61K 31/16* (2006.01)
(52) U.S. Cl. ........ 564/182; 564/158; 564/170; 562/450; 560/41; 514/538; 514/563; 514/617
(58) Field of Classification Search .................. 564/158, 564/170, 182; 562/450; 560/41; 514/538; 514/563, 617
See application file for complete search history.

(56) References Cited

U.S. PATENT DOCUMENTS

| 4,223,016 | A | 9/1980 | Roy et al. | |
|---|---|---|---|---|
| RE37,160 | E | 5/2001 | Kohn et al. | |
| 6,319,492 | B1 * | 11/2001 | Kohn et al. | 424/78.08 |

FOREIGN PATENT DOCUMENTS

| JP | 57-193437 | 11/1982 |
|---|---|---|
| RU | 2233289 C2 | 7/2004 |
| WO | 97/23202 | 7/1997 |

OTHER PUBLICATIONS

Tangpasuthadol, V. et al. "Hydrolytic degradation of tyrosine-derived polycarbonates, a class of new biomaterials. Part I. Study of model compounds", Biomaterials, 2000, v.21(23), p. 2371-2378, coe__. (1), (7).

Stefane, B.,;"3-Acyl-1,3-diaryltriazenes as neutral and selective acylating agents", Tetrahedron Letters, 2001, v.42(38), p. 6659-6662, coe__ 8, 11, 12.
Kotlova, E. K. et al.: "Obrazovanie dipeptidov-pobochnaya reaktsya pri ratsemizatsil fenilalanina", Bioorganicheskaya Khimiya, 1999, vol. 5, No. 9, pp. 652-657.
Basharov, M. A. et al.: Vlyanie bokovykh radikalov na strukturu peptidov. Poverkhnosti potentsialnoi energil modelnykh dipeptidov analiza i fenilalanina, Molekulyarnaya biologya, 1988, vol. 22, issue 5, pp. 1219-1224.
Krupyanko, V. I. et. Nekotorye fiziko-khimicheskie i kineticheskie svoystva metalloproteinazy bakterioliticheskogo preparata lizomidazy:, Biokhimya, 1990, vol. 55, issue 7, pp. 1279-1286, Table 3.
Ljubeznova, M. R. et al.: "Asimmetrichesky sintez aminokislot putem kataliticheskogo vosstanovleniya azlaktonov atsilaminoakrilovykh kislot", Izvestiya Akademil nauk, Seriya khimicheskaya, 1990, No. 4, pp. 811-818, coed. III, p. 817.
Lisichkina, I. N. et al.: "Gidrirovanie proizvodnykh degidroaminokslot v prisutstvii kompleksov palladiya (II) s metioninom", Izvestiya Akademii nauk, Seriya khimicheskaya, 1988, No. 5, pp. 1170-1172.
Shvachkin, Yu.P. et al.:"Natural peptides and their analogs", Biorganicheskaya Khimia, 1985 (Russian), v.11(8), p. 1026-1036, (the abstract) [on-line], Found on the database ACS on STN, CA 104:225198.
Ivanov, G. G. et al. "Vlyanie taurina i dipeptida Tug-Tug na defibrilyatsiju zheludochkov cerdtsa", Bjulleten eksperimentalnoi biologil i meditsiny, 1992, vol. 113(5), pp. 463-464.
Banerjee, Ipsita A., et al.:"From peptide nanospheres to nanorods at interfaces", American Cancer Society, Division of Polymer Chemistry, 2005, 46(2), p. 746-747 (the abstract) [on-line] Found on the database ACS on STN CA 144:274530.
Paquet, Alenka et al.,:"Synthesis of phosphotyrosine-containing peptides using bis-(2,2,2-trichloro)ethyl groups for phosphate protection", Journal of peptide research, 1997, v.50(4), p. 262-268 (the abstract) [on-line] Found on the database ACS on STN, CA 127:307658. Auzeil, Nicholas et al.:"Electrochemical removal of the picolinoyl group under mild acidic conditions", Tetrahedron letters, 1997, v.38(13), p. 2283-2286 & Nosho Yasuharu et al.:"Studies model of bitter including arginine, proline and phenylalanine residues", Agricultural and biological chemistry, 1985, v.49(6), p. 1829-1837 (the abstract) [on-line] Found on the database ACS on STN, CA 126:330844, 103:86669.
Lo, Lee Chiang et al.:"Separation of diastereomers of protected dipeptides by normal-phase high-performance liquid chromatography", Journal of chromatography, 1989, v.472(1), p. 336-339 (the abstract) [on-line] Found on the database ACS on STN, CA 112:131607.
Terada, Shigeyuki et al.:"Action of pepsin on synthetic substrates.", Journal of Biochemistry, 1971, v.70 (1), p. 133-142 (the abstract) [on-line] Found on the database ACS on STN, CA 75:94886.

(Continued)

*Primary Examiner* — Shailendra Kumar
(74) *Attorney, Agent, or Firm* — Banner & Witcoff, Ltd.

(57) ABSTRACT

The present invention relates to novel phenyl-N-acyl derivatives of biogenic amines and amino acids of general formula (I) as cyclooxynease inhibitors, possessing analgetic and antiinflammatory properties and devoid of side effects in particular ulcerogeneity and pro-spasmodic actions, as well as capability to potentiate effect of other analgetics, and possessing in addition antihypoxic, antidepressant and anti-Parkinsonistic action; as well as to the processes for the preparation novel and known phenyl-N-acyl derivatives of biogenic amines, to a pharmaceutical composition and to an agent comprising compounds of general formula (I) as well as to use thereof and a method of treating.

8 Claims, No Drawings

OTHER PUBLICATIONS

Guschina, A.E. et al.:"Structure of pepsin.II.Active site of the enzyme (resolution 2A)", Molekulyarnaya Biologiya, 1985, v.19(1), p. 225-229 (the abstract) [on-line] Found on the database ACS on STN, CA 103:34106.

Karnauchov, E.N. et al.:"Synthesis of peptide fragments of the protein-chromophre binding site in bacteriorhodopsin", 1979, v.9(2), p. 47-54 (the abstract) [on-line] Found on the database ACS on STN, CA 95:62668.

Stepanov, V.M. et al.:"Biospecific chromatography of chymosin", 1976, v.41(2), p. 294-303 (the abstract) [on-line] Found on the database ACS on STN, CA 84:160982.

Kozlov, L.V. et al.:"Effect of pH on the mechanism of action of pepsin", 1973 (Russian), Khim.Proteoliticheskikh Fermentov, Mater.Vses.Simp., Meeting Date 1973, 111, Inst.Biokhim.: Vilnus, USSR, (Russian), 1973 (the abstract) [on-line] Found on the database ACS on STN, CA 82:166598.

Kozlov, L.V. et al.:"Free energy of peptide bond hydrolysis and enzymic sythesis of N-acetyldipeptide esters.", Biokhimiya, 1966, v.31(2), p. 315-321 (the abstract) [on-line] Found on the database SCS on STN, CA 65:22005.

* cited by examiner

US 8,309,766 B2

PHENYL-CONTAINING N-ACYL AMINE AND AMINOACID DERIVATIVES, METHODS FOR THE PRODUCTION THEREOF, A PHARMACEUTICAL COMPOSITION AND THE USE THEREOF

CROSS-REFERENCE TO RELATED APPLICATIONS

This application is a U.S. National Stage application under 35 U.S.C. §371 of International Application PCT/RU2006/000139 (published as WO 2006/101422 A1), filed Mar. 24, 2006 which claims priority to Application RU 2005108492, filed Mar. 25, 2005. Benefit of the filing date of each of these prior applications is hereby claimed. Each of these prior applications is hereby incorporated by reference in its entirety.

This application is a 371 of PCT/GB08/50801, filed 09/08/2008. The present invention relates to the field of bioorganic chemistry and concerns novel *compounds, phenyl*-N-*acyl* derivatives of biogenic amines as well as a process for synthesis of *novel* and known *compounds*, use thereof in medicine as potential *analgetic, anti-inflammatory, spasmolitic* and *anti-hypoxic agents*, as well as agents possessing *anti-depressant, anti-*P*arkinsonistic effect* and ability to potentiate effect of other *analgetics*.

PRIOR ART

The publication of the International application WO 97/23202 discloses phenyl-N-acyl derivatives of amines of general formula (XV)

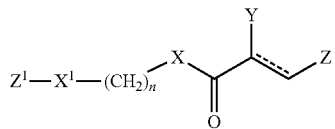

which, among the others, covers 3-(p-hydroxyphenyl)-propionyl phenylethylamine, 3-(p-hydroxyphenyl)-propionyltyramine and 3-phenylpropionyl phenylethylamine (compounds IX, X, XI of the present invention, respectively). This publication discloses synthesis of compounds of general formula (XV) and use thereof as selective ligands of NMDA receptors subtypes useful for treating chronic pain, migraine headache as well as anesthetics. However, the indicated publication does not disclose or characterize specific structures corresponding to compounds X and XI of the present invention and any data supporting the declared activity are missed, and compound IX as an intermediate compound and synthesis thereof are disclosed in the process for preparation of other amines derivatives only.

Compounds IX, X and XI of the instant invention are also disclosed in earlier publications which became generally available to the public before the priority date of the International application WO 97/23202 indicated above, to be used for a different purpose.

3-(p-hydroxyphenyl)-propionyl phenylethylamine (IX) is disclosed in Jacobson K. A., Kirk K. L. New high-performance liquid chromatographic procedure for the detection and quantification of β-phenylethylamine.//J. Chromatography. 1987. V. 415. P. 124-128); 3-(p-hydroxyphenyl)-propionyl tyramine (X) is disclosed in R. B. Herbert, A. E. Kattah. The biosynthesis of Sceletium alkaloids in Sceletium subvelutinum L. Bolus.//Tetrahedron. 1990. V. 46. No 20. P. 7105-7118 and 3-phenyl propionyl phenylethylamine (XI) is disclosed in Maldonado E., Hernandez E., Ortega A. Amides, coumarine and other constituents from Simsia cronquistii.//Phytochem. 1992. P. 1413-1414.

The publication of the International application WO 97/23202 notes the possibility to use compounds of general formula (XV) for preventing some specific kinds of pain such as migraine headache, chronic pain as well as use thereof for anesthesia due to is the ability of said compounds to act as selective ligands of NMDA receptor subtypes. However, WO 97/23202 lacks any data supporting the declared activity of the this group of compounds and thus, the possibility to use such compounds for the indicated purpose on particular in vivo animal models and hence, conclusions about possible pharmacological effects are based exclusively on the assertion that all the compounds disclosed in the indicated International application are selective ligands of NMDA receptor subtypes.

The publication of the International application WO 97/23202 discloses a process for synthesis of 3-(p-hydroxyphenyl)-propionyl phenylethylamine (IX) using 1-hydroxybenzotriazole in the presence of N,N'-dicyclohexylcarbodiimide (DCC). A process for isolating and purifying said compound is not disclosed; among the physical-chemical constants, only melting point and $^1$H-NMR spectroscopy are given.

Article Jackson K. A., Kirk K. L. New high-performance liquid chromatographic procedure for the detection and quantification of β-phenylethylamine.//J. Chromatography. 1987. V. 415. P. 124-128 discloses the synthesis of 3-(p-hydroxyphenyl)-propionyl phenylethylamine (IX) using a modified N-oxysuccinimide ester of 3-(p-hydroxyphenyl)-propionic acid. Reaction is carried out in the mixture methanol—1M $Na_2HPO_4$, pH 8 (1:1), using sulfosuccinimidyl-3-(p-hydroxyphenyl)-propionate (the sulfated Bolton-Hunte reagent). The prepared product is characterized by the melting point only. In accordance with this article, 3-(p-hydroxyphenyl)-propionyl phenylethylamine prepared is used as an internal standard in an electrochemical detector in quantitative determination of intrinsic phenylethylamine level in body fluids using the HPLC method.

Article Herbert R. B., Kattah A. E. The biosynthesis of Sceletium alkaloids in Sceletium subvlutinum L. Bolus.//Tetrahedron. 1990. V. 46. No 20. P. 7105-7118 discloses the use of 3-(p-hydroxyphenyl)-propionyl tyramine (X) as an intermediate in the synthesis of Sceletium subvlutinum alkaloids as well as a process for synthesis thereof using the DCC method. A shortcoming of the instant process is the necessity of using column chromatography for purifying the target product with a comparatively low yield (about 48%).

The article Maldonado E., Hernandez E., Ortega A. Amides, coumarine and other constituents from Simsia cronquistii.//Phytochem. 1992. P. 1413-1414 discloses isolation of 3-phenyl propionyl phenylethylamine (XI) from an overland part of Simsia cronquistii plants and mass spectrometry, $^1$H-NMR spectroscopy data as well as the melting point are presented. No biological activity data are presented.

Synthesis of the compound XI using a condensing agent 4-(4,6-dimethoxy-1.3.5-triasin-2-yl)-4-methylmorpholine chloride (DMT-MM) is disclosed in Kumishima M., Kawachi C., Hioki K. et al. Formation of carboxamides by direct condensation of carboxylic acids and amines in alcohols using a new alcohol- and water-soluble condensing agent: DMT-MM.//Tetrahedron. 2001. V. 57. No 8. P. 1551-1558. A drawback of the given synthesis method is formation of a byproduct and the need in using preparative thin-layer chromatography to purify the target product that complicates the process and must inevitably lead to lowering yields. In spite of this, a high yield of the product (XI) making up 99% is indicated. Compound XI was synthesized to study applicability of the novel condensing agent DMT-MM.

Synthesis of tyrosine and phenylalanine amino acid derivatives such as 3-(p-hydroxyphenyl)-propionyltyrosine, phenylpropionyltyrosine, phenylacetyltyrosine, phenylpropionylalanine and phenylpropionyltyrosine methyl ester (compounds XIV, XV, XVI, XVIII and XX1 of the present invention, respectively) and the study of their inhibiting effect on the TAN neuron identified in the ganglion of Achatina fulica farussae snail are disclosed in the articles Takeuchi H., Ariyoshi Y., Effects of N-beta-phenyl propionyl-L-tyrosine and its derivatives on the excitability of an identifiable giant neuron of Achatina fulica ferussac.//Comparative biochemistry and physiology. C: Comparative pharmacology. 1982. V. 72. No 2. P. 225-229 and Y. Ariyoshi, H. Takeuchi. Structure-activity relationships of N-β-phenylpropionyl-L-tyrosine and its derivatives on the inhibition of an identifiable giant neuron of an African giant snail.//Br. J. Pharmacol. 1982. V. 77. P. 631-639. In the article Y. Ariyoshi, H. Takeuchi. Structure-activity relationships of N-β-phenylpropionyl-L-tyrosine, and its derivatives on the inhibition of an identifiable giant neuron of an African giant snail. 1/Br. J. Pharmacol. 1982. V. 77. P. 631-639. A typical technique of synthesis of compounds XIV, XV, XVI, XVIII and XX1 by the method of activated N-oxysuccinimide esters using as an amine derivative tyrosine methyl ester with subsequent saponification thereof (for compounds XIV, XV, XVI, XVIII) is described, but physicochemical constants and an yields for said compounds are not given. Furthermore, synthesis of phenylacetyltyrosine (XV) with a high yield (94%) using 1-hydroxybenzotriasol and ethyl-3(3-dimethylamino)propylcarbodiimide using as starting compounds tyrosine ethyl ester and phenylpropionic acid with subsequent saponification of ethyl ester is disclosed in Tangpasuthadol V., Pendharkar S. M., Kohn J. Hydrolytic degradation of tyrosine-derived polycarbonates, a class of new biomaterials. Part I: Study of model compounds.//Biomaterials. 2000. V. 21. No 23. P. 2371-2378. $^1$H-NMR spectroscopy and melting point are presented.

Synthesis of phenylpropionyl phenylalanine (XVIII) by the chloroanhydride method in the presence of KOH is disclosed in Lustig N., Spiegelstain-Klarfeld H., Scheider E., Lichtenstein N. Phenylacetyl and phenylpropionyl amino acids. Their inhibitory effect on glutamine synthetase and their resistance to acylase. I.//Israel Journal of Chemistry. 1974. V. 12. No 3. P. 757-763. Melting point and elemental analysis are presented. Synthesis has been carried out to study inhibition degree of glutamine synthetase with compound XVIII.

Phenylpropionyltyrosine methyl ester (XXI) is mentioned in the JP patent 57193437 (Example 4), wherein synthesis thereof is implemented by the method of activated N-oxysuccinimide esters.

Synthesis of phenylacethylphenylalanine (XIX) similar to the synthesis of compound XVIII using chloroanhydride of phenylacetic acid is disclosed in Chen H. M., Hsu M. S., Huang L. J., et al. Effect of N-phenylacetyl L-amino acids on the differentiation of HL-60 cells.//Chinese Pharmaceutical Journal. 2001. V. 53. No 3. P. 157-167. The physicochemical characteristics of the target compound (melting point, $^1$H-NMR- and IR-spectroscopy, mass-spectroscopy) are presented. Phenylacethylphenylalanine (XIX) has been established to be an inductor of cellular differentiation.

3-(p-Hydroxyphenyl)-propionyltyrosine methyl ester (XX) is mentioned in the publication of the International application WO 97/23202, however, synthesis and physicochemical characteristics thereof are not presented. Compound (XX) is synthesized in order to use it as a monomer for the preparation of biodegradable polymers comparable with tissues.

A natural compound isolated from the symbiotic bacterium Xenorhabdus nematophilus, phenylacetylethylamin (XXIII) was synthesized by the chloroanhydride method and characterized by physicochemical data of $^1$H-NMR-, $^{13}$C-NMR- and IR-spectroscopy, mass-spectroscopy, melting point in the publication of the International application WO 01/49656. In vitro anti-tumor activity of compound XXIII has been investigated.

A general formula of the compounds disclosed in the publication of the International application WO 01/49656 covers also the other compounds of the instant invention: p-hydroxyphenylacetyltyramine, p-hydroxyphenylacetylphenylethylamine, and phenylacetyltyramine (compounds VII, VIII and VI of the instant invention, respectively). However, said publication does not disclose neither particular structural formulae of the indicated compounds nor synthesis thereof, nor physicochemical constants, nor biological activity data.

Phenylpropionyltyramine (XII) is mentioned in the article Takeuchi Hiroshi, Tamura Hiroko. The effects of aromatic amino acid derivatives on the excitability of an identifiable giant neuron of an African giant snail (Achatina fulica ferussac).//British Journal of Pharmacology. 1980. V. 69. No 1. P. 29-34, but without disclosure of synthesis thereof and physicochemical characteristics and purpose thereof.

In the article Garrett C. E., Jiang X., Prasad K, Pepic O. New observations on peptide bond formation using CDMT.// Tetrahedron Letters. 2002. V. 43, No 23. p, 4161-4165 phenylpropionylphenylalanine methyl ester (XXIV) and a process for synthesis thereof using the condensing agent 2-chloro-4,6-dimethoxy-1,3,5-triasine (CDMT) in the presence of N-methylmorpholine are disclosed. However, neither physicochemical characteristics of said compound, nor activity data are presented. Only notice as given that the instant process has the following advantages: a one-step synthesis and isolation of the product by precipitating with water results in a chromatographically pure product with a high yield of 90%.

Article Peric M., Vercek B., Petric A. ω-Diazoacetophenones as reagents for a mild and selective protection of an amino group.//Acta Chimica Slovenica. 1996. V. 43. No 2. P. 163-173 discloses synthesis of phenylacetyltyrosine methyl ester (XXII) an intermediate for peptide synthesis by condensation of phenylacetic acid with tyrosine methyl ester through formation of diasoketone. For purifying compound XXII, the use of column chromatography is obligatory. Melting point, $^1$H-NMR-spectroscopy and elemental analysis data are presented.

Phenylacethylphenylalanine methyl ester (XXV) in accordance with Votano J. R., Altman J., Wilchek M., Potential use of biaromatic L-phenylalanyl derivatives as therapeutic agents in the treatment of sickle cell disease.//Proceedings of the National Academy of Sciences of the United States of America. 1984. V. 81. No 10. P. 3190-3194 was synthesized by the method of activated N-oxysuccinimide esters with subsequent purification by column chromatography. Physicochemical constants for said compound are not presented. In this article, compound XXV is an intermediate in synthesis of compound XIX which is being investigated as a candidate agent for treating sickle cell disease.

Furthermore, a method for enzymatic synthesis of compound XXV is known [Didziapetris R., Drabnig B., Schellenberger V., Jakubke H. D., Svedas V. Penicillin acylase-catalyzed protection and deprotection of amino groups as a promising approach in enzymatic peptide synthesis.//FEBS Letters. 1991. V. 287. No 1-2. P. 31-33].

Patent US 2003199566 (Bok S., Lee S., Jeong T., Phenolic acid derivatives and composition for preventing or treating blood lipid level-related diseases comprising the same) discloses a synthesis of 3-(p-hydroxyphenyl)-propionylphenylalanine (XVII) and 3-(p-hydroxyphenyl)-propionylphenylalanine methyl ester (XIII) is using 1-hydroxybenzotriasol and 1-[3-(dimethylamino)propyl]-3-ethylcarbodiimide hydrochloride in the presence of triethylamine. For preparing 3-(p-hydroxyphenyl)-propionylphenylalanine (XVII) saponification of compound (XIII) was further carried out with yield of the target product 78%. For the both compounds, data of $^1$H-NMR- and $^{13}$C-NMR-spectroscopy are presented. Compounds XVII and XIII are proposed to be used for preventing and treating diseases associated with blood level of lipids.

The International application publication WO 9952962 discloses 3-(p-hydroxyphenyl)propionyl-tyrosine benzyl ester (XXXIV). Melting point, data of $^1$H-NMR- and $^{13}$C-NMR-spectroscopy are presented.

Analgetic effect is known to be implemented in accordance with different mechanisms, in particular by inhibiting cyclooxigenase enzyme in the arachidonic acid cascade [Mashkovsky PPM Lekarstvennye sredstva (Medicaments).//Moscow. Novaya volna publishers. 2005. P. 163-164].

Non-narcotic analgetics and non-steroid anti-inflammatory agents possess the most manifested analgetic effect among the drugs lowering synthesis of algogenes. Non-narcotic analgetics are represented by salicilates (aspirin), pyrazolone derivatives (amidopirin, analgin) and para-aminophenol (paracetamol). To non-steroid anti-inflammatory agents belong derivatives of salicylic, acetic, propionic and antranylic acids. Non-narcotic analgetics and non-steroid anti-inflammatory agents along with analgetic effect possess anti-inflammatory and antipyretic action [Kukushkin M. L., Khitrov N. K. Obshchaya patologiya boli (General pathology of pain)/Moscow. Meditsina publishers. 2004. 142 pages]. Ulcerogeneity is the main side effect of non-steroid anti-inflammatory agents. A pro-spasmodic side effect is often observed in analgetics with different mechanism of action [Mashkovsky PPM Lekarstvennye sredstva (Medicaments).// Moscow. Novaya volna publishers. 2005. P. 154].

Anti-Parkinsonistic properties of non-steroid anti-inflammatory drugs sodium salicilate, indomethacine and pyroxycam are known [M. G. Kadieva, E. T. Oganesyan, S. Kh. Matsueva. Nejrotoxiny I sredstva dlya lecheniya bolezni Parkinsona. III. Sredstva, oposredovanno vlijaushchiye na dofaminergicheskuyu sistemu. (Neurotoxines and agents for treating Parkinson's disease. III. Agents with mediated effect on the dopaminergic system). Khimiko-pharmacevticheskij zhurnal. 2005. T. 39. No 11. S. 3-11]. Such activity is supposed to be partially realized being mediated through prostaglandins effecting the dopaminergic system.

Anti-serotonine drugs are also known to exert a positive effect on the dopamine system in Parkinson's disease promoting binding receptors to dopamine antagonists [M. G. Kadieva, E. T. Oganesyan, S. Kh. Matsueva. Nejrotoxiny I sredstva dlya lecheniya bolezni Parkinsona (Neurotoxines and agents for treating Parkinson's disease) Khimiko-pharmacevtichskij zhurnal. 2005. T. 39. No 11. S. 3-11]. There are also other mechanisms of action of anti-Parkinsonistic drugs [Mashkovsky PPM Lekarstvennye sredstva (Medicaments).//Moscow. Novaya volna publishers. 2005. P. 138].

Depending on mechanism of action, antidepressants are subdivided into several groups, in particular monoamine oxydase inhibitors, tricyclic antioxidants, blockers of histamine, serotonin, cholecystokinin α-adrenoreceptors [Mashkovsky PPM Lekarstvennye sredstva (Medicaments).//Moscow. Novaya volna publishers. 2005. P. 109].

Since the use of the known antidepressants and structurally related compounds is accompanied by numerous serious side effects, then search for novel safe and efficient drugs having such action is actual. The use of the compounds of the present invention for preventing and treating depressive conditions was unknown.

Hypoxia is observed in numerous pathological states including disorders of the brain functions. Antioxidants improve utilization of circulating oxygen by the body enhancing resistance of the body to oxygen deficit. Drugs having such action are not numerous [Mashkovsky PPM Lekarstvennye sredstva (Medicaments).//Moscow. Novaya volna publishers. 2005. P. 729]. Many drugs including those controlling activity of the CNS additionally possess anti-hypoxic properties enhancing efficacy of their action. For the group of compounds of the present invention, anti-hypoxic effect had not been earlier disclosed.

An object of the present invention is synthesis and use of novel and known phenyl-N-acyl derivatives of biogenic amines and amine acids as non-toxic, more efficient analgetics and anti-inflammatory agents without side effects, in particular ulcerogeneity and pro-spasmodic action, which also possess anti-hypoxic, antidepressant and anti-Parkinsonistic action as well as capability to potentiate effect of other analgetics.

SUMMARY OF THE INVENTION

The present invention relates to novel phenyl-N-acyl derivatives of amines of general formula I:

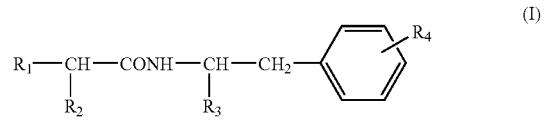

wherein $R_1$ is

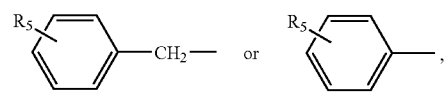

where $R_5$ is hydrogen or hydroxy group;
$R_2$ is hydrogen or amino group optionally substituted with $CH_3(CH_2)_mCO-$, where m is 0 to 4; $R_3$ is hydrogen, $-COOH$, $-COOR_6$, wherein $R_6$ is $C_1$-$C_6$ alkyl or

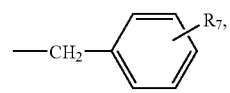

wherein $R_7$ is hydrogen or hydroxy group,
$R_4$ is hydrogen or hydroxy group;
with proviso that the compound of general formula I is not phenylacetyltyramine, 3-(p-hydroxyphenyl)propionylphenylethylamine,
3-(p-hydroxyphenyl)propionyltyramine,
3-phenylpropionylphenylethylamine,
3-phenylpropionyltyramine,
3-(p-hydroxyphenyl)propionylphenylalanine methyl ester,
3-(p-hydroxyphenyl)propionyltyrosine,
3-phenylpropionyltyrosine,
phenylacetyltyrosine,
3-(p-hydroxyphenyl)propionylphenylalanine,
3-phenylpropionylphenylalanine,
phenylacetylphenylalanine,
3-(p-hydroxyphenyl)propionyltyrosine methyl ester,
3-phenylpropionyltyrosine methyl ester,
phenylacetyltyrosine methyl ester,
phenylacetylphenylethylamine,
3-phenylpropionylphenylalanine methyl ester,
phenylacetylphenylalanine methyl ester,
3-(p-hydroxyphenyl)propionyl-tyrosine benzyl ester;

or pharmaceutically acceptable salts thereof possessing cyclooxygenase-inhibiting activity, anti-inflammatory and analgetic action, spasmolitic, anti-hypoxic, anti-Parkinsonistic and antidepressant action as well as capability to potentiate effect of other analgetics.

The present invention also relates to the use of compounds of general formula I:

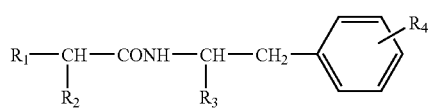
(I)

wherein $R_1$ is

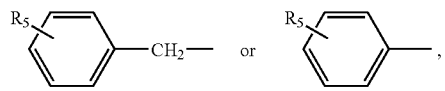

where $R_5$ is hydrogen or hydroxy group;

$R_2$ is hydrogen or amino group optionally substituted with $CH_3(CH_2)_mCO-$, where m is 0 to 4; $R_3$ is hydrogen, —COOH, —COOR$_6$, where $R_6$ is $C_1$-$C_6$ alkyl or

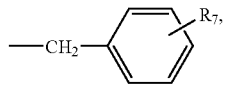

wherein $R_7$ is hydrogen or hydroxy group, $R_4$ is hydrogen or hydroxy group or pharmaceutically acceptable salts thereof as cyclooxygenase-inhibitors, analgetic and anti-inflammatory, spasmolitic, anti-hypoxic, anti-Parkinsonistic and antidepressant agents as well as agents capable to potentiate effect of other analgetics.

Further, the present invention relates to a pharmaceutical composition or an agent possessing cyclooxygenase-inhibiting activity, anti-inflammatory and analgetic action, as well as antidepressant, spasmolitic, anti-hypoxic, anti-Parkinsonistic action, containing an effective amount of the compound of formula I or pharmaceutically acceptable salts thereof and optionally a pharmaceutically acceptable carrier.

Another subject-matter of the invention is a method for treating pain syndromes of different genesis as well as diseases accompanied by inflammation, spasms, hypoxia, depression and parkinsonism signs, comprising administration of an effective amount of the compound of general formula I or a pharmaceutically acceptable salt thereof optionally in combination with other analgetics.

The present invention also relates to novel processes for preparing compounds of general formula I.

DETAILED DISCLOSURE OF THE INVENTION

Preferable compound of formula I are compounds wherein $R_3$ is —COOH, —COOCH$_3$.

Novel preferable compound of formula I are presented in Table 1.

TABLE 1

| Compound | No of compound | $R_1$ | $R_2$ |
|---|---|---|---|
| HO—⟨⟩—CH$_2$—CO—NH—CH(COOH)—CH$_2$—⟨⟩—OH<br>p-hydroxyphenylacetyltyrosine | II | ⟨⟩—OH | H |
| HO—⟨⟩—CH$_2$—CO—NH—CH(COOH)—CH$_2$—⟨⟩<br>p-hydroxyphenylacetylphenylalanine | III | ⟨⟩—OH | H |
| HO—⟨⟩—CH$_2$—CO—NH—CH(COOCH$_3$)—CH$_2$—⟨⟩—OH<br>p-hydroxyphenylacetyltyrosine methyl ester | IV | ⟨⟩—OH | H |

TABLE 1-continued

| Structure | # | R group | R' |
|---|---|---|---|
| HO–⟨benzene⟩–CH₂–CO–NH–CH(COOCH₃)–CH₂–⟨benzene⟩<br>p-hydroxyphenylacetylphenylalanine methyl ester | V | —⟨benzene⟩–OH | H |
| HO–⟨benzene⟩–CH₂–CO–NH–CH₂–CH₂–⟨benzene⟩–OH<br>p-hydroxyphenylacetyltyramine | VII | —⟨benzene⟩–OH | H |
| HO–⟨benzene⟩–CH₂–CO–NH–CH₂–CH₂–⟨benzene⟩<br>p-hydroxyphenylacetylphenylethylamine | VIII | —⟨benzene⟩–OH | H |
| HO–⟨benzene⟩–CH₂–CO–NH–CH(COOBzl)–CH₂–⟨benzene⟩–OH<br>p-hydroxyphenylacetyltyrosine benzyl ester | XXVI | —⟨benzene⟩–OH | H |
| HO–⟨benzene⟩–CH₂–CO–NH–CH(COOBzl)–CH₂–⟨benzene⟩<br>p-hydroxyphenylacetylphenylalanine benzyl ester | XXVII | —⟨benzene⟩–OH | H |
| CH₃–CO–NH–CH(CH₂–⟨benzene⟩–OH)–CO–NH–CH₂–CH₂–⟨benzene⟩<br>acetyltyrosylphenylethylamine | XXVIII | —CH₂–⟨benzene⟩–OH | CH₃–CO–NH |
| CH₃–CO–NH–CH(CH₂–⟨benzene⟩–OH)–CO–NH–CH₂–CH₂–⟨benzene⟩–OH<br>acetyltyrosyltyramine | XXIX | —CH₂–⟨benzene⟩–OH | CH₃–CO–NH |
| ⟨benzene⟩–CH₂–CH₂–CO–NH–CH(COOBzl)–CH₂–⟨benzene⟩–OH<br>3-phenylproponyltyrosine benzyl ester | XXX | —CH₂–⟨benzene⟩ | H |
| ⟨benzene⟩–CH₂–CO–NH–CH(COOBzl)–CH₂–⟨benzene⟩–OH<br>phenylacetyltyrosine benzyl ester | XXXI | —⟨benzene⟩ | H |
| HO–⟨benzene⟩–CH₂–CH₂–CO–NH–CH(COOBzl)–CH₂–⟨benzene⟩<br>3-(p-hydroxyphenyl)-propionylphenylalanine benzyl ester | XXXII | —CH₂–⟨benzene⟩–OH | H |

TABLE 1-continued

| Compound | No of compound | R₃ | R₄ |
|---|---|---|---|
| phenylpropionylphenylalanine benzyl ester: C₆H₅—CH₂—CH₂—CO—NH—CH(COOBzl)—CH₂—C₆H₅ | XXXIII | —CH₂—C₆H₅ | H |
| p-hydroxyphenylacetyltyrosine: HO—C₆H₄—CH₂—CO—NH—CH(COOH)—CH₂—C₆H₄—OH | II | —COOH | —OH |
| p-hydroxyphenylacetylphenylalanine: HO—C₆H₄—CH₂—CO—NH—CH(COOH)—CH₂—C₆H₅ | III | —COOH | H |
| p-hydroxyphenylacetyltyrosine methyl ester: HO—C₆H₄—CH₂—CO—NH—CH(COOCH₃)—CH₂—C₆H₄—OH | IV | —COOCH₃ | —OH |
| p-hydroxyphenylacetylphenylalanine methyl ester: HO—C₆H₄—CH₂—CO—NH—CH(COOCH₃)—CH₂—C₆H₅ | V | —COOCH₃ | H |
| p-hydroxyphenylacetyltyramine: HO—C₆H₄—CH₂—CO—NH—CH₂—CH₂—C₆H₄—OH | VII | H | —OH |
| p-hydroxyphenylacetylphenylethylamine: HO—C₆H₄—CH₂—CO—NH—CH₂—CH₂—C₆H₅ | VIII | H | H |
| p-hydroxyphenylacetyltyrosine benzyl ester: HO—C₆H₄—CH₂—CO—NH—CH(COOBzl)—CH₂—C₆H₄—OH | XXVI | —C(=O)—O—CH₂—C₆H₅ | —OH |
| p-hydroxyphenylacetylphenylalanine benzyl ester: HO—C₆H₄—CH₂—CO—NH—CH(COOBzl)—CH₂—C₆H₅ | XXVII | —C(=O)—O—CH₂—C₆H₅ | H |
| acetyltyrosylphenylethylamine: CH₃—CO—NH—CH(CH₂—C₆H₄—OH)—CO—NH—CH₂—CH₂—C₆H₅ | XXVIII | H | H |

TABLE 1-continued

| Compound | No of compound | $R_1$ | $R_2$ |
|---|---|---|---|
| acetyltyrosyltyramine | XXIX | H | —OH |
| 3-phenylproponyltyrosine benzyl ester | XXX | —C(=O)O—CH$_2$—C$_6$H$_5$ | —OH |
| phenylacetyltyrosine benzyl ester | XXXI | —C(=O)O—CH$_2$—C$_6$H$_5$ | =OH |
| 3-(p-hydroxyphenyl)-propionylphenylalanine benzyl ester | XXXII | —C(=O)O—CH$_2$—C$_6$H$_5$ | H |
| phenylpropionylphenylalanine benzyl ester | XXXIII | —C(=O)O—CH$_2$—C$_6$H$_5$ | H |

The known preferable compounds of formula I are presented in Table 2.

| Compound | No of compound | $R_1$ | $R_2$ |
|---|---|---|---|
| phenylacetyltyramine | VI | —C$_6$H$_5$ | H |
| 3-(p-hydroxyphenyl)-propionylphenylethylamine | IX | —CH$_2$—C$_6$H$_4$—OH | H |
| 3-(p-hydroxyphenyl)-propionyltyramine | X | —CH$_2$—C$_6$H$_4$—OH | H |
| 3-phenylpropionylphenylethylamine | XI | —CH$_2$—C$_6$H$_5$ | H |

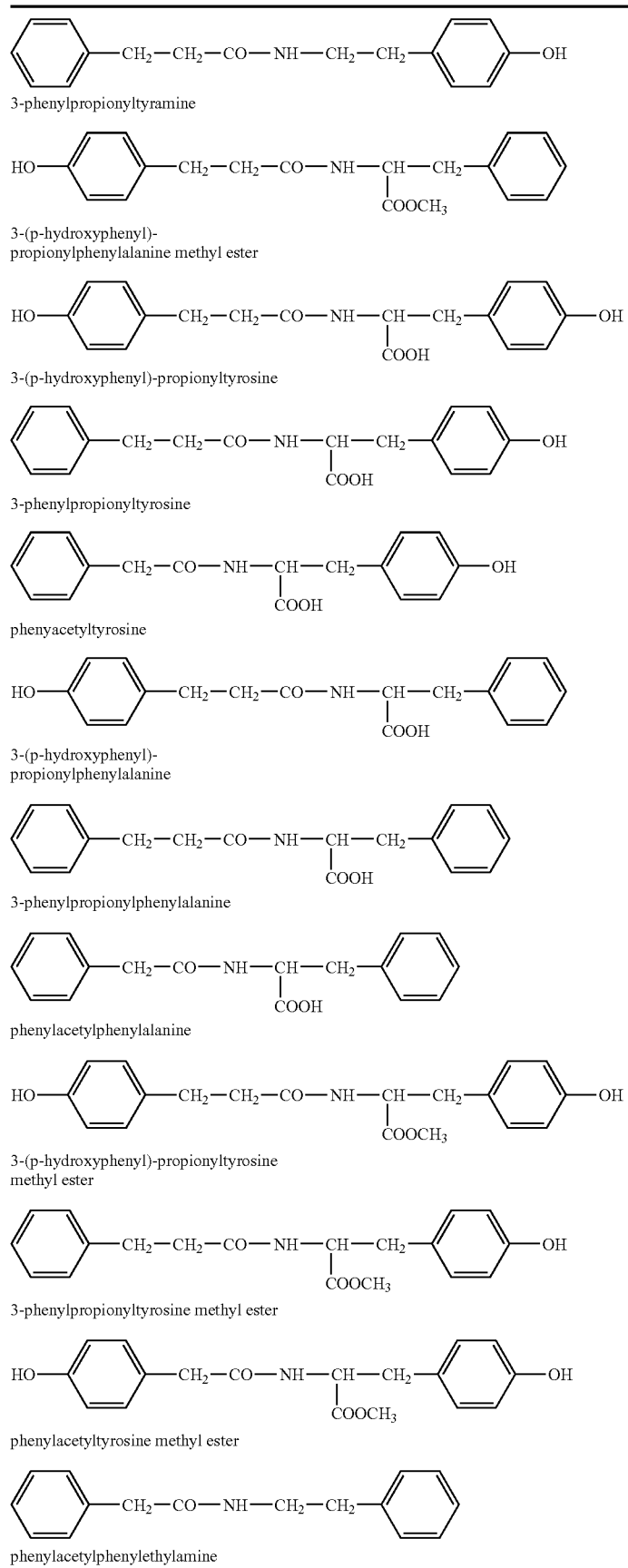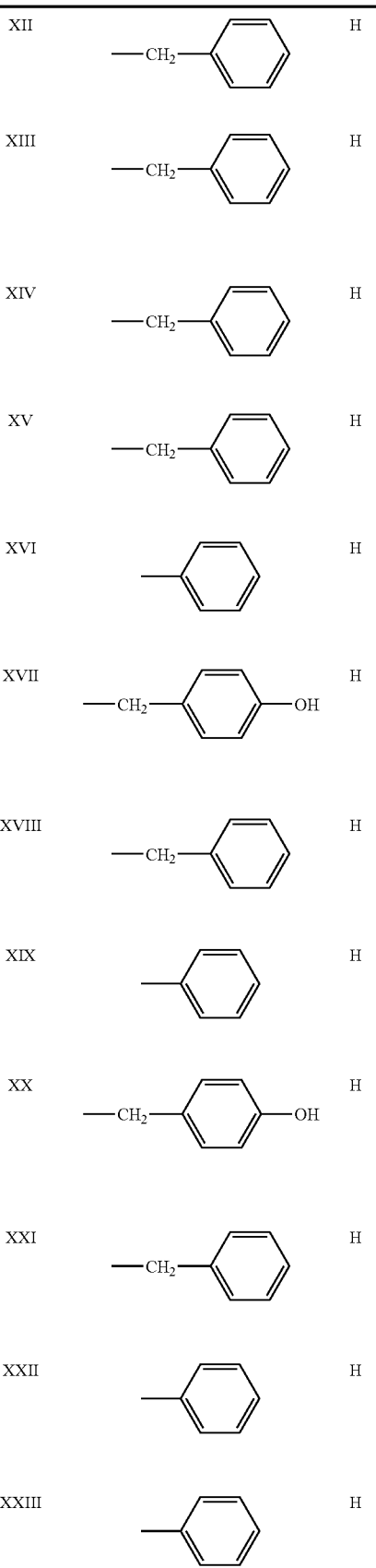

-continued

| Compound | No of compound | | |
|---|---|---|---|
| 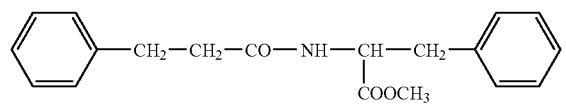<br>3-phenylpropionylphenylalanine methyl ester | XXIV | 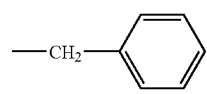 | H |
| 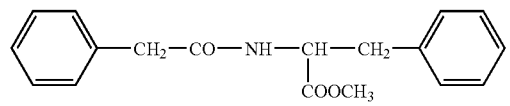<br>phenylmethylphenylalanine methyl ester | XXV | 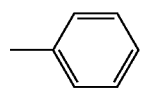 | H |
| 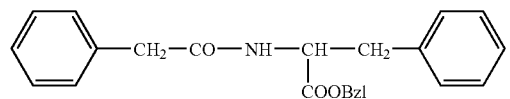<br>phenylmethylphenylalanine benzyl ester | XXXV | 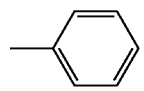 | H |
| 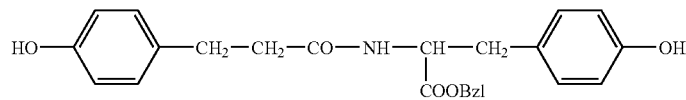<br>3-(p-hydroxyphenyl)-propionyltyrosine benzyl ester | XXXIV | 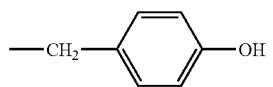 | H |

| Compound | No of compound | $R_3$ | $R_4$ |
|---|---|---|---|
| 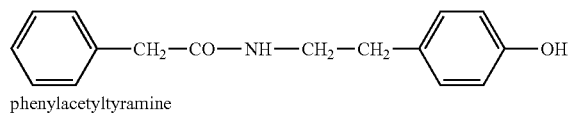<br>phenylacetyltyramine | VI | H | —OH |
| 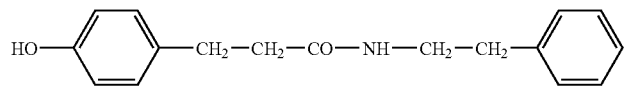<br>3-(p-hydroxyphenyl)-propionylphenylethylamine | IX | H | H |
| 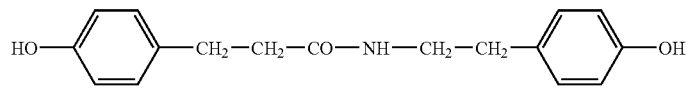<br>3-(p-hydroxyphenyl)-propionyltyramine | X | H | —OH |
| 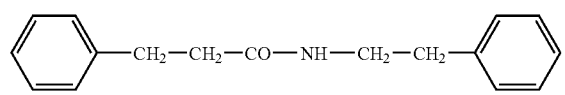<br>3-phenylpropionylphenylethylamine | XI | H | H |
| 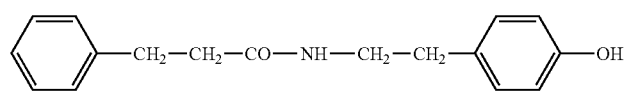<br>3-phenylpropionyltyramine | XII | H | —OH |
| 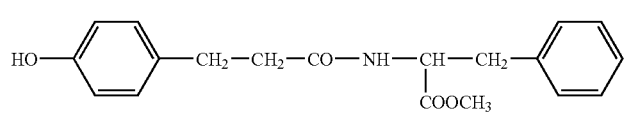<br>3-(p-hydroxyphenyl)-propionylphenylalanine methyl ester | XIII | —COOCH$_3$ | H |
| 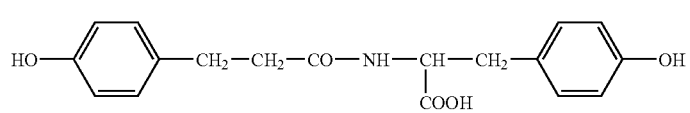<br>3-(p-hydroxyphenyl)-propionyltyrosine | XIV | —COOH | —OH |

-continued

| | | | |
|---|---|---|---|
| 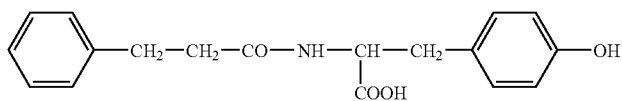<br>3-phenylpropionyltyrosine | XV | —COOH | —OH |
| 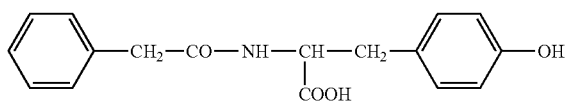<br>phenyacetyltyrosine | XVI | —COOH | —OH |
| 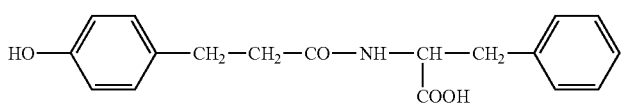<br>3-(p-hydroxyphenyl)-propionylphenylalanine | XVII | —COOH | H |
| 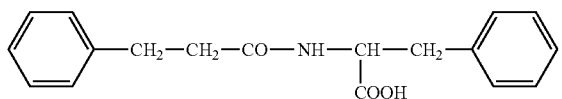<br>3-phenylpropionylphenylalanine | XVIII | —COOH | H |
| 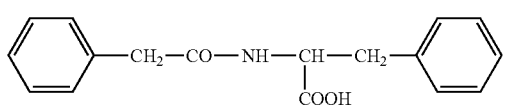<br>phenylacetylphenylalanine | XIX | —COOH | H |
| 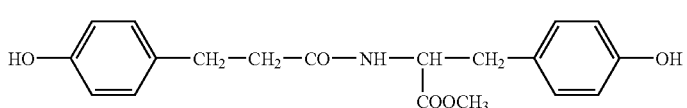<br>3-(p-hydroxyphenyl)-propionyltyrosine methyl ester | XX | —COOCH₃ | —OH |
| 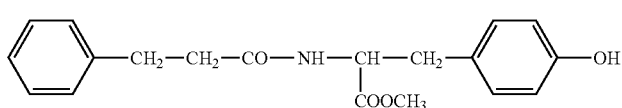<br>3-phenylpropionyltyrosine methyl ester | XXI | —COOCH₃ | —OH |
| 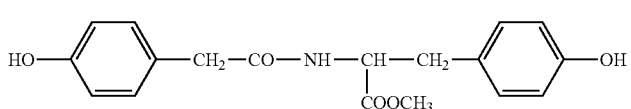<br>phenylacetyltyrosine methyl ester | XXII | —COOCH₃ | —OH |
| 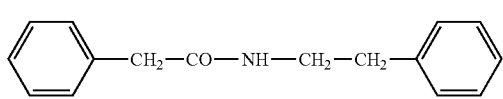<br>phenylacetylphenylethylamine | XXIII | H | H |
| 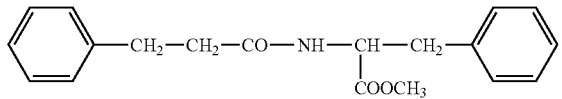<br>3-phenylpropionylphenylalanine methyl ester | XXIV | —COOCH₃ | H |
| 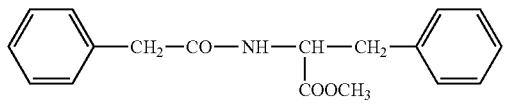<br>phenylmethylphenylalanine methyl ester | XXV | —COOCH₃ | H |

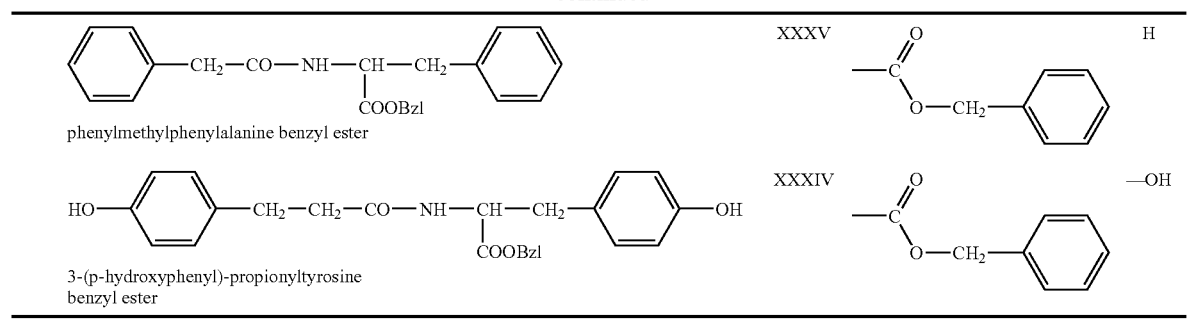

phenylmethylphenylalanine benzyl ester 3-(p-hydroxyphenyl)-propionyltyrosine benzyl ester Compounds of general formula I are prepared by activation of a carboxyl group of p-hydroxyphenylacetic acid or phenylacetic acid by reacting with diphenylphosphorylazide (DPPA) and triethylamine (TEA) in an organic solvent, preferably N,N-dimethylformamide, ethylacetate at cooling preferably at the temperature ranging from −25° to 0°, followed by reacting with an amino derivative. Preferably, activation of carboxy group is implemented using 1-1.2 equivalents of DPPA and TEA. As an amino derivative, tyrosine and phenylalanine esters may be used. For preparing compounds II and III, as a starting amino derivative, tyrosine and phenylalanine benzyl esters are used respectively, followed by the removal of benzyl group by catalytic hydrogenolysis. Unlike the earlier used synthesis methods of the known compounds of formula I, the use if the diphenylphosphorylazide method allowed to decrease the number of steps, namely to delete the step of isolating an activated derivative of carboxylic component, to be restricted by extraction for isolating target substances and to increase yields ($\geqq 90\%$).

A general scheme of synthesis by the diphenylphosphorylase method is presented in Scheme 1.

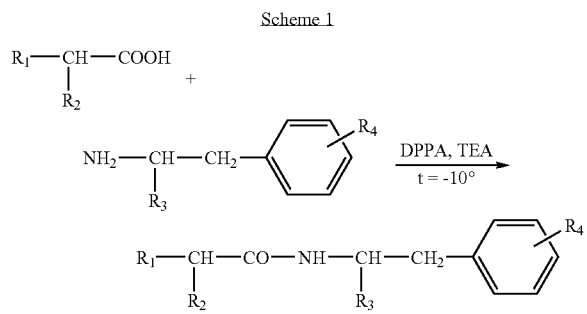

Scheme 1

Novel compounds II, III, IV, V, VII, VIII including those comprising hydroxy substituent in phenyl groups, can be also prepared using the method of activated N-oxysuccinimide esters, advantage of which is availability of reagents, water-solubility of released N-hydroxysuccinimide, fast running of both reaction of preparing N-oxysuccinimide esters of acylating agents and reaction of amide bond formation, and the possibility of achieving high yields of the target products (70-80%) in spite of the presence of hydroxy substituent in phenyl group. In accordance with the proposed process, synthesis of N-oxysuccinimide esters of acylating agents is realized by converting p-hydroxyphenylacetic acid or phenylacetic acid into activated N-oxysuccinimide ester using the N,N'-dicyclohexylcarbodiimide method (DCC-method) with a high yield (about 90%) and subsequent formation of amide bond by reaction between N-oxysuccinimide esters and an amino derivative, also with high yields (70-80%) for a short time (1-2 hours) and without using chromatographic purification of the target product. As an amino derivative, tyrosine and phenylalanine esters may be used. Similarly, the known compounds X, XI, XII, XIII, XV, XVII, XIX, XX, XXII, XXIII, XXIV can be prepared, synthesis of which using the method of activated N-oxysuccinimide esters is not disclosed in the prior art.

A general synthesis scheme of compounds of general formula I using the method of activated N-oxysuccinimide esters is presented in Scheme 2.

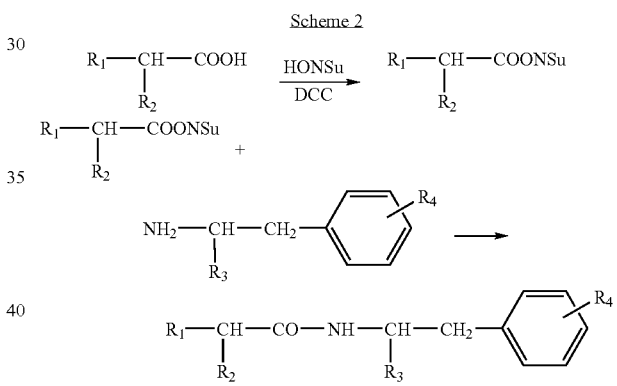

Scheme 2

Synthesis of hydroxyphenylpropionyltyrosine (XIV) may be also implemented using the method of activated N-oxysuccinimide esters, unprotected C-terminal tyrosine being possibly used in order to decrease the number of steps. Furthermore, this allows avoid a prolonged exposure to alkali, which would be necessary for saponification of tyrosine methyl ester that could have been unfavorably reflected on optic purity of the target compound [Schreder E., Lübke K.//Peptidy (Peptides)./Moscow. "Mir" publishers. 1967. 2 volumes; Gross E., Meienhoffer I.//Peptidy. Osnovniye metody obrazovanija peptidnoj svyazi (Peptides. Main formation methods of peptide bond)/Moscow. "Mir" publishers. 1983. p. 422]. The problem of a low solubility of unprotected tyrosine in both organic solvents and water is solved by transition thereof into a soluble sodium salt resulting from addition to tyrosine suspension in DMF of two equivalents of 1N NaOH solution that resulted in observed complete dissolution of the amino acid. Reaction between thus obtained solution of the amino derivative with N-oxysuccinimide ester of 3-(p-hydroxyphenyl)propionic acid occurs practically completely and quickly (for 2 hours). Following isolation by extraction without application of chromatographic purification, yield of the target product (XIV) made up about 63%.

Compounds of general formula I can be also prepared in the form of pharmaceutically acceptable addition salts with non-toxic acids such as fumaric acid, maleic acid, succinic acid, acetic acid, citric acid, tartaric acid and the like and salts with bases such as sodium hydroxide, potassium hydroxide, sodium carbonate and the like.

Compounds of general formula I possess cyclooxygenase inhibiting activity and are useful for treating pain syndromes of different genesis, inflammatory and inflammatory-degenerative diseases of joints and connective tissue as well as the skeletal-muscular system, different diseases accompanied by inflammation, spasms, hypoxia, to potentiate other analgetics as well as disorders caused by depression and Parkinson's disease.

In particular, compounds of the present invention may be used for treating postoperative pain, posttraumatic pain as well as pain syndromes of gynecological, neurological, cancerous, dental origin, rheumatoid arthritis, arthropathy, Bekhterev's disease, non-specific spondylloarthritis, gout arthritis, osteoarthrosis, extraarticular rheumatic fever and thrombophlebitis, other diseases accompanied by inflammation, spasms, hypoxia as well as disorders caused by Parkinson's disease, emotional-stress states.

Compounds of the present invention are administered in an effective amount which provides for desirable therapeutic result.

Compounds of formula (I) can be administered orally, topically, parenterally, by inhalations and rectally in the form of unit dosage forms comprising non-toxic pharmaceutically acceptable carriers. "Parenteral administration" as used herein means subcutaneous, intravenous, intramuscular or intraperitoneal injections or infusions.

Compounds of the present invention can be administered to a patient at doses from 0.1 to 10 mg/kg body weight daily, preferably at doses 0.5 to 5 mg/kg once or more times daily.

At the same time, it should be noted that a particular dose for every individual patient will depend on many factors including activity of a given compound used, age, body weight, sex, general health condition of patient and his nutrition regimen and mode of administering a medicament, elimination rate, a particular combination of medicaments used as well as severity of disease being treated.

Pharmaceutical compositions according to the present invention comprise a compound according to the present invention in an amount effective to achieve desirable result and they may be administered as unit dosage forms (for example in a solid, semi-solid or liquid forms) comprising compounds of the present invention as an active ingredient in a mixture with a carrier or excipient suitable for intramuscular, intravenous, oral, sublingual, inhalation and intrarectal administration. Active ingredient may be included into the composition together with usually used non-toxic pharmaceutically acceptable carriers suitable for preparing solutions, tablets, pellets, capsules, dragee, suppositoria, emulsions, suspensions, ointments, gels and any other dosage forms.

As excipients, different substances may be used such as saccharides, e.g. glucose, lactose or sucrose, mannitol or sorbitol, cellulose derivatives and/or calcium phosphates, e.g. tricalcium phosphate or acidic calcium phosphate; as a binder, may be used such substances as a starch paste, e.g. corn, wheat, rise, potato starch, gelatin, tragacant, methylcellulose, hydroxypropylmethylcellulose, sodium carboxymethylcellulose and/or polyvinylpyrrolidone. When necessary, disintegrants may be used such as the above mentioned starches and carboxymethylstarch, cross-linked polyvinylpyrrolidone, agar or alginic acid or a salt thereof such as sodium alginate.

Optional additives such as agents regulating fluidity and lubricants such as silica dioxide, talc, stearic acid and salts thereof such as magnesium stearate or calcium stearate and/or propyleneglycol may be used.

A dragee core is usually coated by a layer, which is resistant to action of gastric juice. For this purpose, concentrated solutions of saccharides may be used which may optionally comprise gum Arabic, talc, polyvinylpyrrolidone, polyethyleneglycol and/or titanium dioxide and suitable organic solvents or mixtures thereof.

As additives, stabilizers, thickeners, dyes and flavors may be also used.

As an ointment base, carbohydrate ointment bases such as white and yellow Vaseline (Vaselinum album, Vaselinum flavum), Vaseline ointment (Oleum Vaselini), white and yellow ointment (Unguentum album, Unguentum flavum), and as additives for imparting a more compact consistence additives such as hard paraffin and wax may be used; absorptive ointment bases such as hydrophilic Vaseline (Vaselinum hydrophylicum), lanoline (Lanolinum), coldcreme (Unguentum leniens) may be used; ointment bases washable by water such as hydrophilic ointment (Unguentum hydrophylicum) may be used; water-soluble ointment bases such as polyethyleneglycol ointment (Unguentum Glycolis Polyethyleni), bentonite bases and other may be used.

As a base for gels, methylcellulose, carboxymethylcellulose sodium salt, oxypropylcellulose, polyethyleneglycol or polyethylene oxide, carbopol may be used.

As a base for suppositoria, bases insolvable in water such as cocoa butter;

bases soluble in water or mixable with water such as gelatin-glycerol or polyethylene oxide; combine bases, e.g. saponaceous-glycerinic bases may be used.

In manufacturing a unit dosage form, an amount of active ingredient used in a combination with a carrier may vary depending on recipient being treated, a particular mode of administering a medicament.

Thus for example, in using compounds of the present invention in the form of solutions for injections, content of the active agent therein is 0.01-5%. As dilutors, 0.9% sodium chloride solution, distilled water, novocaine solution for injections, Ringer solution, glucose solution, specific additives for dissolution may be used. In administering compounds of the present invention into the body in the form of tablets and suppositoria, their amount is 5.0-500 mg per an unit dosage form.

Dosage forms of the present invention are manufactured according to standard techniques such as e.g. processes of mixing, granulation, formation of dragee, dissolution and freeze drying.

It should be noted that compounds of the present invention manifest biological activity at doses which are by two-three orders lower as compared to the known drugs used for comparison, at practically similar efficacy, and for them, no negative side effects have been revealed and contraindication for use thereof have not been found. At the same time, in studying toxicity of compounds of the present invention at an oral dose of 1000 μg/kg, death of experimental animals has not been recorded.

A detailed description of compounds of the present invention, preparation thereof and examination of their pharmacological activity are presented below in the following examples designed to illustrate preferred variants of the invention and not limiting the scope thereof.

EXAMPLES OF SYNTHESIS OF COMPOUNDS OF THE PRESENT INVENTION

Individuality of the prepared compounds was checked using TLC method on the plates "Kiesegel 60 $F_{254}$"

("Merck", Germany) in the following system of solvents: chloroform-methanol 9:1 (1), chloroform-methanol-ethyl acetate 6:1:3 (2), chloroform-methanol-ammonia 6:3:0.5 (3).

Chromatograms were developed with chloro-tolidine reagent, ninhydrin, iodine and by luminescence in UV light.

$^1$H-NMR was recorded on the apparatus "AMX-400 Bruker" (Germany).

IR-Fourier spectra were taken in KBr tablets on the apparatus "Magna 750" ("Nicolet" USA).

Melting points was determined on the apparatus "Boetius" (Germany).

High resolution mass spectra were obtained on a transit-time mass spectrometer by the method of matrix laser-desorption ionization using as a matrix 2,5-dihydrobenzoic acid on the apparatus REFLEX™ III (Bruker, Germany).

Analytical reverse phase HPLC was carried out on the apparatuses:

the chromatograph "Breeze", the detector "Waters" (USA), detection at 214 nm, elution rate 1 ml/min under the following conditions (1): the column Symmetry 300 $C_{18}$, 3.9×150 mm, 5 µm, elution with 0.1% aqueous TFA with acetonitrile gradient of from 0% to 60% for 18 minutes;

the chromatograph "System Gold" (:Beckman", USA), elution rate 0.25 ml/min, detection at 220 nm under the following conditions (2): the column "Phenomenex" (USA) $C_{18}$, 2×250 mm, 5 µm, elution with 0.1% aqueous TFA with 0.08% TFA gradient in 100% MeCN from 0% to 100% for 50 minutes.

the chromatograph "Breeze", the detector "Waters" (USA), detection at 214 nm, elution rate 1 ml/min under the following conditions (3): the column Symmetry 300 $C_{18}$, 4.6×250 mm, 20 µm, elution with 0.1% TFA with gradient of 0.09% TFA in the mixture 60:40 acetonitrile-water of from 0% to 100% for 15 minutes.

EXAMPLE 1 p-Hydroxyphenylacetyltyramine (VII)

Technique A

To a solution of 0.40 g (2.63 mmole) of p-hydroxyphenylacetic acid in 3.5 ml DMF 0.35 g (2.63 mmole) was added while stirring. The solution was cooled down to −10° C. and 0.68 ml (3.16 mmole) diphenylphosphorylazide and 0.44 ml (3.16 mmole) triethylamine were added. The solution was stirred for two hours at −10° C. and left at 20° C. for 15 hours. To the reaction mass 35 ml water were added and extracted with 20 ml ethylacetate. Ethylacetate layer was washed with 10 ml 5% $Na_2CO_3$ solution, water up to pH 7, with 10 ml 5% HCl solution, water up to pH 7. Ethylacetate layer was dried over $Na_2SO_4$, $Na_2SO_4$ was filtered off, ethylacetate was removed under vacuum. Oily residue was triturated with ester-hexane mixture (1:1). The formed white precipitate was filtered off and dried under vacuum over $CaCl_2$. Yield 0.68 g (95%).

$R_f$ 0.7 (1).

$T_m$=147-149°.

[M]$^+$271.6.

$^1$H-NMR, $CD_3OD$, δ, ppm: 2.65 (t, J=7 Hz, 2H, α-$CH_2$-TA), 3.29-3.32 (m, 4H, β-$CH_2$-TA, $CH_2$—(OH-PhAc)), 6.63-6.75 (m, 4H, o-CH-arom.), 6.90-7.06 (m, 4H, m-CH-arom.).

IR-Fourier, cm$^{-1}$: 3276 (val. OH); 3108 (val., =C—H, arom.); 1612 (amide I); 1591 (amide II); 1515 (arom. —C—C—); 1226 (val., —C—O, phenolic).

Found, %: C, 70.57; H, 6.43; N, 5.50; $C_{16}H_{17}NO_3$.

Calculated, %: C, 70.83; H, 6.32; N, 5.16.

HPLC under the conditions (1): an individual peak, retention time 8.71 minutes.

Technique B

To a solution of 0.70 g (4.60 mmole) of p-hydroxyphenylacetic acid in 17 ml ethylacetate 0.53 g (4.60 mmole) N-hydroxysuccinimide was added while stirring, the solution was cooled down to 0° C. and 0.95 g (4.60 mmole) N,N'-dicyclohexylcarbodiimide (DCC) was added. The solution was stirred for two hours at 0° C. and left at 4° C. for 20 hours. Precipitate of N,N'-dicyclohexylurea (DCU) was filtered off. Solvent was removed under vacuum. Oily residue was triturated with hexane. The formed white solid precipitate was filtered off, washed with hexane and dried under vacuum over $CaCl_2$. Yield was 1.08 g (94.6%). $R_f$ 0.58 (1).

To a solution of 0.30 g (1.2 mmole) N-oxysuccinimide ester of p-hydroxyphenylacetic acid in 8 ml N,N-dimethylformamide (DMF) 0.16 g (1.2 mmole) tyramine was added while stirring. The reaction mixture was stirred for two hours at 20° C., left at 4° C. for 20 hours. DMF was removed under vacuum. Oily residue was triturated with water. The formed white precipitate was filtered off, washed with water. Yield 0.26 g (80%).

$R_f$ 0.68 (1).

$T_m$=146-148°.

[M+H]$^+$ 272.3.

Found, %: C, 71.05; H, 6.10; N, 5.25; $C_{16}H_{17}NO_3$. Calculated, %: C, 70.83; H, 6.32; N, 5.16.

EXAMPLE 2 p-Hydroxyphenylacetylphenylethylamine (VIII)

Synthesis was carried out in accordance with technique A presented for compound VII.

Yield 0.57 g (90.5%).

$R_f$ 0.82 (1).

$T_m$=69-70°.

[M]$^+$ 255.5.

$^1$NMR DMSO-$d_6$, δ, ppm: 2.68 (t, J=8 Hz, 2H, β-$CH_2$—PEA), 3.22-3.26 (m, α-$CH_2$—PEA), 3.36 (s, 2H, $CH_2$—(OH-PhAc)), 6.66 (d, J=4 Hz, 2H, m-CH-arom. OH-PhAc), 7.00 (d, J=4 Hz, 2H, m-CH-arom. OH-PhAc), 7.14-7.28 (m, 5H, arom. —CH-PEA), 8.0 (br. s, 1H, NH—PEA), 9.20 (s, 1H, OH—(OH-PhAc)).

IR-Fourier, cm$^{-1}$: 3332 (val. OH); 3087 (val., =C—H, arom.); 1626 (amide I); 1558 (amide II); 1515 (arom. —C—C—); 1249 (val., —C—O, phenolic).

Found, %: C, 75.57; H, 6.80; N, 5.77; $C_{16}H_{17}NO_2$. Calculated, %: C, 75.27; H, 6.71; N, 5.49.

HPLC under the conditions (1): an individual peak, retention time 11.17 minutes.

Synthesis was carried out in accordance with technique B presented for compound VII.

Yield 0.50 g (79.4%).

$R_f$ 0.85 (1).

$T_m$=68-70°.

[M]+255.7.

Found, %: C, 75.17; H, 6.87; N, 5.75; $C_{16}H_{17}NO_2$. Calculated, %: C, 75.27; H, 6.71; N, 5.49.

EXAMPLE 3

3-(p-Hydroxyphenyl)-propionyltyramine (X)

Synthesis was carried out in accordance with technique A presented for compound VII.

Yield 0.41 g (95%).
$R_f$ 0.38 (1).
$T_m$=174-176°.
$^1$NMR DMSO-$d_6$, δ, ppm: 2.26 (t, J=8 Hz, 2H, α-CH$_2$—(HO-PhPr)), 2.53 (t, J=6 Hz, 2H, β-CH$_2$-Tyra), 2.67 (t, J=8 Hz, 2H, β-CH$_2$—(HO-PhPr)). 3.16 (t, J=6 Hz, 2H, α-CH$_2$-Tyra), 6.62 (d, J=7 Hz, 2H, m-CH-Bzl-Tyra), 6.65 (d, J=7 Hz, m-CH-Bzl-(HO-PhPr)), 6.92-6.96 (m, 4H, o-CH-Bzl-Tyra and o-CH-Bzl-(HO-PhPr)), 7.79 (s, 1H, NH-Tyra), 9.09 (br. s, 2H, OH-Tyra and OH—(HO-PhPr)).

IR-Fourier, cm$^{-1}$: 3249 (val. OH); 1621 (amide I); 1515 (arom.); 1541 (amide II).

Found, %: C, 71.56; H, 6.78; N, 4.97; $C_{16}H_{17}NO_2$. Calculated, %: C, 71.56; H, 6.71; N, 4.91, $C_{17}H_{19}NO_3$.

HPLC under the conditions (2): an individual peak, retention time 25.62 minutes.

Synthesis was carried out in accordance with technique B presented for compound VII.

Yield 0.37 g (85%).
$R_f$ 0.35 (1).
$T_m$=172-174°.
[M]$^+$285.3.

EXAMPLE 4

3-Phenylpropionylphenylethylamine (XI)

Synthesis was carried out in accordance with technique A presented for compound VII.

Yield 0.26 g (97%).
$R_f$ 0.78 (1).
$T_m$=94-96°.
$^1$NMR DMSO-$d_6$, δ, ppm: 2.34 (t, J=8 Hz, 2H, α-CH$_2$—(HO-PhPr)), 2.66 (t, J=6 Hz, 2H, β-CH$_2$—PEA), 2.79 (t, J=8 Hz, 2H, O—CH$_2$-PhPro)), 3.24 (t, J=6 Hz, 2H, α-CH$_2$—PEA), 7.25-7.30 (m, 10H, CH-arom.), 7.89 (br. s, 1H, NH—PEA).

IR-Fourier, cm$^{-1}$: 1637 (amide I); 1546 (amide II).

Found, %: C, 80.24; H, 7.61; N, 5.54. Calculated, %: C, 80.60; H, 7.56; N, 5.53, $C_{17}H_{19}NO_3$.

HPLC under the conditions (2): an individual peak, retention time 37.86 minutes.

Synthesis was carried out in accordance with technique B presented for compound VII.

Yield 0.20 g (77%).
$R_f$ 0.80 (1).
Found, %: C, 80.39; H, 7.53; N, 5.30. Calculated, %: C, 80.60; H, 7.56; N, 5.53, $C_{17}H_{19}NO_3$.

EXAMPLE 5

3-(p-Hydroxyphenyl)-propionylphenylethylamine (IX)

Synthesis was carried out in accordance with technique A presented for compound VII.

Yield 0.20 g (90%).
$R_f$(II) 0.4.
$T_m$=102-104°. Cast. [84] 102-104°.
[M]$^+$ 269.6.

$^1$NMR CDCl$_3$, δ, ppm: 2.39 (t, J=7 Hz, 2H, α-CH$_2$—(HO-PhPr)), 2.73 (m, 2H, β-CH$_2$—PEA), 2.86 (t, J=7 Hz, 2H, β-CH$_2$—(HO-PhPr)), 3.48 (m, 2H, α-CH$_2$—PEA), 6.75 (m, 2H, m-CH-arom. HO-PhPr), 7.03 (m, 2H o-CH-arom. HO-PhPr), 7.09 (m, 2H, o-CH-arom. PEA), 7.3 (m, 3H, m,p-CH-arom. PEA).

IR-Fourier, cm$^{-1}$: 3263 (val. OH); 1618 (amide I); 1537 (amide II).

Found, %: C, 75.57; H, 6.93; N, 5.09. $C_{17}H_{19}NO_2$. Calculated, %: C, 75.81; H, 7.11; N, 5.20.

HPLC under the conditions (3): an individual peak, retention time 14.77 minutes.

EXAMPLE 6 p-Hydroxyphenylacetyltyrosine Methyl Ester (IV)

Synthesis was carried out in accordance with technique A presented for compound VII.

Yield 0.17 g (39%).
$R_f$ 0.56 (2).
[M]$^+$ 329.85.
$[α]_D^{25}$+12.22° (C, 0.36; MeOH).
$^1$NMR DMSO-$d_6$, δ, ppm: 2.78 (dd, 1H, CH$_2$-Tyr), 2.9 (dd, 1H, CH$_2$-Tyr), 3.25-3.45 (m, 2H, CH$_2$—HOPhAc), 4.3-4.4 (m, 1H, α-CH-Tyr), 3.6 (s, 3H, OCH$_3$ Tyr), 6.55-7.1 (m, 8H, arom. H), 8.25 (d, 1H, NH-Tyr).

IR-Fourier, δ, cm$^{-1}$: 1649 (amide I); 1515 (amide II); 1263 (amide III).

Found, %: C, 65.75; H, 5.75; N, 4.23. Calculated, %: C, 65.64; H, 5.81; N, 4.25.

HPLC under the conditions (3): an individual peak, retention time 7.25 minutes.

EXAMPLE 7 p-Hydroxyphenylacetylphenylalanine Methyl Ester (V)

Synthesis was carried out in accordance with technique A presented for compound VII.

Yield 0.40 g (39%), oil.
$R_f$ 0.70 (2).
[M]$^+$ 313.83.
$[α]_D^{20}$+35.05° (C, 0.19; ethyl acetate).
$^1$NMR DMSO-d6, δ, ppm: 2.9 (dd, 1H, CH$_2$-Phe), 3.05 (dd, 1H, CH$_2$-Phe), 3.25-3.4 (m, 2H, CH$_2$—HOPhAc), 3.6 (s, 3H, OCH$_3$ Phe), 4.4-4.5 (m, 1H, α-CH-Phe), 6.55-6.95 (m, 4H, arom. H HOPhAc), 7.1-7.3 (m, 5H, arom. H Phe), 8.3 (d, 1H, NH-Phe), 9.2 (s, 1H, OH—Ar HOPhAc).

IR-Fourier, δ, cm$^{-1}$: 1663 (amide I); 1515 (amide II); 1263 (amide III).

Found, %: C, 69.08; H, 6.05; N, 4.45. Calculated, %: C, 68.99; H, 6.11; N, 4.47.

HPLC under the conditions (3): an individual peak, retention time 8.57 minutes.

EXAMPLE 8

Phenylacetyltyramine (VI)

Synthesis was carried out in accordance with technique A presented for compound VII.

Yield 0.35 g (37.6%).
$R_f$ 0.85 (2).
$T_m$ 105-108°.
[M+1]$^+$ 256.2.

¹NMR DMSO-d₆, δ, ppm: 2.6 (t, 2H, α-CH₂-TA), 3.2 (q, 2H, β-CH₂-TA), 3.4 (s, 2H, CH₂-PhAc), 6.6-7.0 (m, 4H, arom. H TA), 7.15-7.3 (m, 5H, arom. H PhAc), 8.0 (t, 1H, NH-TA), 9.1 (s, 1H, OH-TA).

IR-Fourier, δ, cm⁻¹: 1646 (amide I); 1516 (amide II); 1264 (amide III).

Found, %: C, 75.37; H, 6.69; N, 5.45. Calculated, %: C, 75.27; H, 6.71; N, 5.49.

HPLC under the conditions (3): an individual peak, retention time 8.06 minutes.

EXAMPLE 9

3-(p-Hydroxyphenyl)-propionylphenylalanine Methyl Ester (XIII)

Synthesis was carried out in accordance with technique A presented for compound VII.

Yield 0.37 g (38%), oil.
$R_f$ 0.73 (2).
[M+1]⁺ 328.21.
$[α]_D^{25}$ −6.95° (C, 0.46; MeOH).
¹NMR DMSO-d₆, δ, ppm: 2.3 (t, 2H, 1-CH₂ HOPhPr), 2.6 (t, 2H, 2-CH₂ HOPhPr), 2.85 (dd, 1H, CH₂-Phe), 3.0 (dd, 1H, CH₂-Phe), 3.6 (s, 3H, OCH₃ Phe), 4.4-4.5 (m, 1H, α-CH-Phe), 6.6-6.95 (m, 4H, arom. H HOPhPr), 7.15-7.3 (m, 5H, arom. H Phe), 8.22 (d, 1H, NH-Phe), 9.1 (s, 1H, OH—Ar HOPhAc).

IR-Fourier, δ, cm⁻¹: 1651 (amide I); 1516 (amide II); 1266 (amide III).

Found, %: C, 69.61; H, 6.49; N, 4.29. Calculated, %: C, 69.71; H, 6.47; N, 4.28.

HPLC under the conditions (3): an individual peak, retention time 8.9 minutes.

EXAMPLE 10 p-Hydroxyphenylacetyltyrosine Benzyl Ester (XIII)

Synthesis was carried out in accordance with technique A presented for compound VII.

Yield 0.59 g (55.7%), oil.
$R_f$ 0.57 (2).
[M+1]⁺ 406.0.
$[α]D^{20}$ −9.18° (C, 0.20; MeOH).
IR-Fourier, δ, cm⁻¹: 1649 (amide I); 1515 (amide II); 1737 (val C═O ester).

Found, %: C, 71.05; H, 5.70; N, 3.43. Calculated, %: C, 71.10; H, 5.72; N, 3.45.

EXAMPLE 11 p-Hydroxyphenylacetyltyrosine (II)

To solution of 0.59 g (1.47 mole) p-hydroxyphenylacetyltyrosine benzyl ester in 10 ml methanol 0.20 g 10% palladium on coal were added and under vigorous stirring hydration was carried out in hydrogen flow for 1.5 hours. The catalyst was filtered off. Solvent from filtrate was removed under vacuum. Oily residue was triturated with an ester-hexane mixture (1:1). The formed white precipitate was filtered off and dried under vacuum over CaCl₂ and P₂O₅. 0.32 g were obtained (68%).

Yield 37%.
$R_f$ 0.28 (3).
[M+1]⁺ 316.07.
$[α]_D^{25}$ +28.03° (C, 0.31; MeOH).
¹NMR DMSO-d₆, δ, ppm: 2.75 (dd, 1H, CH₂-Tyr), 2.9 (dd, 1H, CH₂-Tyr), 3.2-3.4 (m, 2H, CH₂—HOPhAc), 4.3-4.4 (m, 1H, α-CH-Tyr), 6.55-7.1 (m, 8H, arom.), 8.05 (d, 1H, NH-Tyr).

IR-Fourier, δ, cm⁻¹: 1614 (amide I); 1516 (amide II); 1254 (amide III).

Found, %: C, 64.65; H, 5.41; N, 4.37. C₁₇H₁₇NO₅; Calculated, %: C, 64.75; H, 5.43; N, 4.44.

HPLC under the conditions (1): an individual peak, retention time 6.33 minutes.

EXAMPLE 12 p-Hydroxyphenylacetylphenylalanine Benzyl Ester (XXVII)

Synthesis was carried out in accordance with technique A presented for compound VII.

Yield 0.76 g (74%).
$R_f$ 0.87 (2).
[M+1]⁺ 390.1.
$[α]_D^{20}$ −19.47° (C, 0.19; MeOH).
IR-Fourier, δ, cm⁻¹: 1649 (amide I); 1515 (amide II); 1737 (val C═O ester).

Found, %: C, 74.12; H, 5.92; N, 3.57. Calculated, %: C, 74.02; H, 5.95; N, 3.60.

EXAMPLE 13 p-Hydroxyphenylacetylphenylalanine (III)

To solution of 0.65 g (1.67 mole) p-hydroxyphenylacetylphenylalanine benzyl ester in 10 ml methanol 0.30 g 10% palladium on coal were added and under vigorous stirring hydration was carried out in hydrogen flow for 1.5 hours. The catalyst was filtered off. Solvent was removed from filtrate under vacuum. Oily residue was triturated with an ester-hexane mixture (1:1). The formed white precipitate was filtered off and dried under vacuum over CaCl₂ and P₂O₅. 0.27 g (53%) were obtained.

Yield 39.2%.
$R_f$ 0.42 (3).
[M+1]⁺ 300.09.
$[α]_D^{25}$ +18.57° (C, 0.44; MeOH).
¹NMR DMSO-d₆, δ, ppm: 2.85 (dd, 1H, CH₂-Phe), 3.1 (dd, 1H, CH₂-Phe), 3.2-3.35 (m, 2H, CH₂—HOPhAc), 4.4-4.5 (m, 1H, α-CH-Phe), 6.55-6.95 (m, 4H, arom. H HOPhAc), 7.1-7.3 (m, 5H, arom. H Phe), 8.15 (d, 1H, NH-Phe).

IR-Fourier, δ, cm⁻¹: 1611 (amide I); 1512 (amide II).
Found, %: C, 68.30; H, 5.68; N, 4.65.
Calculated, %: C, 68.21; H, 5.72; N, 4.68.

HPLC under the conditions (3): an individual peak, retention time 7.59 minutes.

EXAMPLE 14

3-Phenylpropionyltyrosine Benzyl Ester (XXX)

Synthesis was carried out in accordance with technique A presented for compound VII.

Yield 0.94 g (70%).
$R_f$ 0.72 (1).
[M]⁺ 403.5.
$[α]_D^{20}$ −11.93° (C, 0.18; MeOH).

Found, %: C, 74.22; H, 6.92; N, 3.57. Calculated, %: C, 74.42; H, 6.25; N, 3.47.

EXAMPLE 15

Acetyltyrosylphenylethylamine (XXVIII)

Synthesis was carried out in accordance with technique A presented for compound VII.
Yield 0.36 g (50%).
$R_f$ 0.57 (1).
$[M]^+$ 326.9.
$[\alpha]_D^{20}$ −9.060 (C, 0.30; MeOH).
IR-Fourier, $\delta$, cm$^{-1}$: 1651 (amide I); 1616 (amide II).
Found, %: C, 69.22; H, 6.52; N, 8.27. $C_{24}H_{23}NO_4$; Calculated, %: C, 69.92; H, 6.79; N, 8.58.

EXAMPLE 16

Acetyltyrosyltyramine (XXIX)

Synthesis was carried out in accordance with technique A presented for compound VII.
Yield 0.77 g (65%).
$R_f$ 0.41 (1).
$[M]^+$ 342.7.
Found, %: C, 66.25; H, 6.32; N, 8.25. $C_{24}H_{23}NO_4$; Calculated, %: C, 66.65; H, 6.48; N, 8.18.

Biological Activity Tests

EXAMPLE 17

Study of the In Vitro Effect of Compounds of General Formula I on [$^{14}$C]arachidonic Acid Metabolism in a Cell-Free Homogenate of Murine Pulmonary Tissue Studies of arachidonic acid metabolism was carried out on females CBA mice who where fed a standard vivarium fodder. Animals (mice) were sacrificed, lungs were extracted, homogenized in a glass homogenizer manufactured by the firm "Wheaton" (USA) at 4° C. in 10 volumes of 0.05 M Tris-HCl buffer. Aliquots (0.5 ml) of supernatant were incubated in 0.5 μCi [1-$C^{14}$]-arachidonic acid [$C^{14}$]-AA, "Amersham", England; specific activity 50-60 μCi/mmole) at 37° C. for 30 minutes. Non-metabolized [$\alpha C^{14}$]-AA and products of metabolism thereof were extracted in 20 volumes of chloroform and methanol mixture (1:1) in extraction efficacy not less than 90% assessed using [$C^{14}$]-PGF$_{2\alpha}$. [$C^{14}$]-AA and metabolites thereof were separated and identified using TLC (the plates Kieselgel 60 of the "Merck" firm, Germany) using as an organic phase, the system of solvents (ethylacetate, isooctane, acetic acid, water—110:50:20:100) and labeled standards. Densitometry of autoradiochromograms obtained on the X-ray film X-Omat AR ("Kodak", USA) and HS 11 ("ORWO", Germany), was performed on the densiscan KS 3 ("Kipp and Zonnen", Holland). Quantitative analysis of individual eicosanoids was carried out using radiometry of fractions obtained by high-performance liquid chromatography (the HPLC-system of the "Gilson" form, France; the column ZORBAX C8 of the "Du Pont" firm, USA) and by elution of spots on TLC-plates. The tested compounds were administered at concentration 10$^{-4}$ M.

The data obtained are presented in Table 3.

TABLE 3

In vitro effect of compounds of general formula I on [$^{14}$C]arachidonic acid metabolism in a cell-free homogenate of murine pulmonary tissue

| No of compound | 6-keto-PGF$_{1\alpha}$ | PGF$_{2\alpha}$ | TXB$_2$ | PGE$_2$ | AA | Prostanoids |
|---|---|---|---|---|---|---|
| IX | −30 | −27 | −40 | −38 | +47 | −33 |
| X | −9 | −15 | −42 | −38 | +27 | −22 |
| XIV | −24 | −24 | −49 | −54 | +84 | −35 |
| XII | | −42 | | −47 | +42 | −44 |
| VII | | −45 | | −32 | +22 | −40 |
| VIII | | −45 | | −33 | +40 | −40 |

PG—prostaglandins
TX—thromboxane
AA—arachidonic acid

The data on eicosanoid profile obtained demonstrate the capability of compounds of general formula I to inhibit cyclooxygenase by 22-44% and suggest that they are promising as potential analgetic and anti-inflammatory agents.

EXAMPLE 18

Analgetic and Anti-Inflammatory Activity of Compounds of General Formula (I) Study of Analgetic Activity on the Model "Acetic Contortions"

The tests were conducted on males of white mongrel mice weighing 22-24 grams. The specific pain response ("contortions") were elicited by intraperitoneal administration to mice of 0.75% acetic acid solution. The following signs were taken into consideration: the number of seizure contractions of abdominal muscles accompanied by stretching the hind limbs and sagging the back. Analgetic effect was assessed by decrease in the number of contortions in animals in percent to the control for 15 minutes post administration of acetic acid. The technique of the tests is disclosed in Koster R., Anderson M., de Beer B.//Fed. Proc. 1959. V. 18. P. 412. Compounds under testing were administered intraperitoneally (using a probe) at a dose 10 μg/kg 60 minutes prior to injection of the acid. Diclofenac (10 mg/kg) was used as a reference drug. Analgetic effect was calculated according to the formula:

$$\frac{Ck - Co}{Co} \times 100.0 (\%)$$

wherein Ck is the number of contortions in the control group,
Co is the number of contortions in the test group.
The data obtained are presented in Table 4.

TABLE 4

Analgetic activity of the tested compounds of general formula I at a dose 10 mg/kg in the "acetic contortion" test (the number of contortions for 15 minutes)

| Compound | Number of mice | C ± m | C, % to the control | Analgetic effect (%) |
|---|---|---|---|---|
| II | 10 | 24.2 ± 1.9* | 75.2 | 24.8 |
| III | 8 | 19.4 ± 3.3* | 60.2 | 39.9 |
| Control 1 | 19 | 32.2 ± 1.6 | 100 | — |
| IV | 10 | 20.8 ± 1.9* | 77.9 | 22.1 |

TABLE 4-continued

Analgetic activity of the tested compounds of general formula
I at a dose 10 mg/kg in the "acetic contortion" test
(the number of contortions for 15 minutes)

| Compound | Number of mice | C ± m | C, % to the control | Analgetic effect (%) |
|---|---|---|---|---|
| V | 10 | 16.2 ± 2.6* | 60.7 | 39.3 |
| Control 2 | 10 | 26.7 ± 0.79 | 100 | — |
| VIII | 8 | 16.0 ± 4.5 | 43.5 | 56.5 |
| Control 3 | 8 | 36.8 ± 3.5 | 100 | — |
| IX | 8 | 11.8 ± 2.9 | 32 | 68 |
| Control 4 | 8 | 36.8 ± 3.5 | 100 | — |
| X | 8 | 11.0 ± 2.4* | 46.0 | 54 |
| Diclofenac 10 µg/kg | 8 | 12.9 ± 2.13* | 50.8 | 49.2 |
| Control 5 | 8 | 25.4 ± 2.4 | 100 | 0 |
| XI | 10 | 21.2 ± 2.5** | 61.8 | 38.2 |
| XII | 10 | 20.1 ± 2.1** | 58.6 | 41.4 |
| Control 6 | 9 | 34.3 ± 3.0 | 100 | — |
| VI | 8 | 21.1 ± 1.8* | 74.5 | 25.5 |
| XIII | 8 | 14.6 ± 1.8** | 51.6 | 48.4 |
| Voltaren 8 µg/kg | 8 | 15.8 ± 2.6* | 55.5 | 44.5 |
| Control 7 | 8 | 28.4 ± 2.5 | 100 | — |
| XXVI | 8 | 22.4 ± 2.0* | 73 | 27 |
| XXVII | 9 | 20.1 ± 1.7* | 67.4 | 32.6 |
| Control 8 | 9 | 29.8 ± 2.3 | 100 | — |
| XXX | 8 | 11.9 ± 1.7** | 63.9 | 36.1 |
| Control 9 | 8 | 18.6 ± 1.4 | 100 | — |
| XXVIII | 9 | 15.9 ± 2.4* | 57.9 | 42.1 |
| XXIX | 10 | 15.7 ± 1.9* | 57.1 | 42.9 |
| Control 10 | 9 | 27.4 ± 2.6 | 100 | — |

*P < 0.05 versus the control group
**P < 0.01 versus the control group

The compounds corresponding to the general formula I show in the "contortion" analgetic activity which is close to that of the reference drugs Diclofenac and Voltaren (see Table 4), analgetic effect of a majority of the compounds being from 38 to 68%

EXAMPLE 19

The Effect of Compounds of General Formula I on Analgetic Action of Tramal and Analgin on the Model "Acetic Contortions"

The studies were carried out in accordance with the technique presented in Example 18.

TABLE 5

The effect of compounds of general formula I at a dose
10 mg/kg on analgetic action of Tramal (10 mg/kg)

| Number of mice | Number of contortions for 15 minutes | | | |
|---|---|---|---|---|
| n = 10 | Control | IX | Tramal | IX + Tramal |
| M ± m | 36.2 ± 3.8 | 24.0 ± 3.4* | 17.5 ± 2.3* | 6.4 ± 2.0*~ |
| Analgetic effect, % | | 33.6 | 53 | 82 |

*statistically significant versus the control group, p < 0.05
~statistically significant versus Tramal, p < 0.05

According to the data of Table 5, analgetic effect of the combination of compound IX with Tramal is significantly more potent than the effect of compounds IX and Tramal alone (6.4±2.0 versus 24.0±3.4 and 17.5±2.3 respectively).

TABLE 6

The effect of compounds of general formula I at a
dose 10 mg/kg on analgetic action of Analgin (50
mg/kg) In the "acetic contortion" test

| Number of mice n = 10 | Number of contortions for 15 minutes | | | |
|---|---|---|---|---|
| | Control | IX | Analgin | IX + Analgin |
| M ± m | 33.1 ± 2.9 | 18.8 ± 3.1* | 20.7 ± 2.3* | 12.6 ± 2.4*~ |
| Analgetic effect, % | | 43.3 | 37.5 | 61.9 |

*statistically significant versus the control group, p < 0.05
~statistically significant versus Tramal, p < 0.05

Compound IX also enhances analgetic action of Analgin (Table 6).

Thus, compound IX at a dose 10 mg/kg in intraventricular administration significantly enhances analgetic action of Tramal and potentiates analgetic effect of Analgin.

EXAMPLE 20

Study of Analgetic Activity on the Model "a Hot Plate"

Analgetic action of the compounds corresponding to general formula I was studies using the "hot plate" model according to the technique presented in Woolfe G., McDonald A. D.//The evaluation of the analgetic action of pethidine hydrochloride (Demerol).//Pharmacol. Exp. Ther. 1944. V. 80. P. 300-307. The tests were conducted on males of white mongrel mice weighing 22-24 grams. The animals were individually placed on a hot plate (manufactured by the firm "Ugo Basile"), a temperature of which remained constant and was equal to 55° C. The following first manifestations of pain reaction were recorded: licking paws, jumping up prior to administration of a substance (background parameters) and 0.5, 1, 2, 3 and 4 hours post administration of a substance. Substances were administered intraventricularly (using a probe). A weighed amount of a substance was thoroughly mixed in 0.1 ml Tween 80 until a solution was obtained, then normal saline was added up to a volume of 0.5 ml. Average latent time of nociception threshold (NT) was calculated in every group. The results obtained were expressed in percent of the background values. Analgetic effect (in %) was calculated according to the formula:

$A-100\%=X$, wherein A is a background parameter; X is analgetic effect (in %)

A is (time 0.5 to 4 hours post administration×100%): background time

As reference drugs, Analgin (150 mg/kg), Paracetamol (200 mg/kg), Ketorol (10 mg/kg), were used.

The data obtained are presented in Table 7.

TABLE 7

Comparative assessment of analgetic action of compounds of general formula I at a dose 10 mg/kg and the reference drugs Analgin and Paracetamol, in the "hot plate" test in mice by the value of latent time of nociception threshold (NT seconds)

| Number of mice n = 10 | 0 (background) | Time post administration of a compound, minutes | | | | |
|---|---|---|---|---|---|---|
| | | 30 | 60 | 120 | 180 | 240 |
| Compound II | | | | | | |
| M ± m | 3.4 ± 0.3 | 6.0 ± 0.6* | 6.1 ± 0.8* | 7.3 ± 0.6** | | |
| Latent time of NT (%) | 100 | 176.5 | 179.4 | 214.7 | | |
| Analgesia (%) | | 76.5 | 79.4 | 114.7 | | |
| Compound III | | | | | | |
| M ± m | 3.7 ± 0.3 | 6.7 ± 0.9* | 5.9 ± 0.8* | 7.0 ± 0.6** | | |
| Latent time of NT (%) | 100 | 181.0 | 159.5 | 189.2 | | |
| Analgesia (%) | | 81.0 | 59.5 | 89.2 | | |
| Compound IV | | | | | | |
| M ± m | 5.03 ± 0.16 | 5.24 ± 0.88 | 5.54 ± 0.32 | 5.93 ± 0.59 | | |
| Latent time of NT (%) | 100 | 104.2 | 110.1 | 117.9 | | |
| Analgesia (%) | | 4.2 | 10.1 | 17.9 | | |
| Compound V | | | | | | |
| M ± m | 3.74 ± 0.16 | 4.85 ± 0.39* | 5.9 ± 0.81* | 6.58 ± 0.72* | | |
| Latent time of NT (%) | 100 | 129.7 | 157.8 | 175.9 | | |
| Analgesia (%) | | 29.7 | 57.8 | 75.9 | | |
| Compound VI | | | | | | |
| M ± m | 5.9 ± 0.4 | 7.8 ± 0.8* | 8.3 ± 1.0* | 6.8 ± 0.5 | | |
| Latent time of NT (%) | 100 | 132.2 | 140.7 | 115.3 | | |
| Analgesia (%) | | 32.2 | 40.7 | 15.3 | | |
| Compound VII | | | | | | |
| M ± m | 5.1 ± 0.49 | | 6.9 ± 0.72 | 8.2 ± 0.94** | | |
| Latent time of NT (%) | 100 | | 134.5 | 158.9 | | |
| Analgesia (%) | | | 34.5 | 58.9 | | |
| Compound VIII | | | | | | |
| M ± m | 5.1 ± 0.49 | | 8.5 ± 0.27** | 6.5 ± 1.16 | | |
| Latent time of NT (%) | 100 | | 159.6 | 123.3 | | |
| Analgesia (%) | | | 59.6 | 23.3 | | |
| Compound IX | | | | | | |
| M ± m | 4.14 ± 0.25 | 8.4 ± 1.23** | 7.36 ± 1.04** | 9.83 ± 2.52** | | 7.72 ± 0.24** |
| Latent time of NT (%) | 100 | 202.9 | 177.8 | 237.0 | | 186.5 |
| Analgesia (%) | | 102.9 | 77.8 | 137.0 | | 86.5 |
| Compound X | | | | | | |
| M ± m | 4.3 ± 0.25 | 7.54 ± 0.78** | 5.75 ± 0.83 | 8.50 ± 1.03** | | 8.84 ± 0.925** |
| Latent time of NT (%) | 100 | 175.3 | 133.7 | 197.7 | | 200.6 |
| Analgesia (%) | | 75.3 | 33.8 | 97.7 | | 100.6 |
| Compound XI | | | | | | |
| M ± m | 3.73 ± 0.19 | 5.35 ± 0.98 | 6.49 ± 1.1** | | 6.27 ± 0.33 | 4.07 ± 0.26 |
| Latent time of NT (%) | 100 | 143.4 | 174.0 | | 141.3 | 135.9 |
| Analgesia (%) | | 43.4 | 74.0 | | 41.3 | 35.9 |
| Compound XIII | | | | | | |
| M ± m | 5.5 ± 0.4 | 5.9 ± 0.3 | 6.7 ± 0.7 | 6.8 ± 0.3* | | |
| Latent time of NT (%) | 100 | 107.3 | 121.8 | 123.6 | | |
| Analgesia (%) | | 7.3 | 21.8 | 23.6 | | |

TABLE 7-continued

Comparative assessment of analgetic action of compounds of general formula I at a dose 10 mg/kg and the reference drugs Analgin and Paracetamol, in the "hot plate" test in mice by the value of latent time of nociception threshold (NT seconds)

| Number of mice n = 10 | 0 (background) | Time post administration of a compound, minutes | | | | |
|---|---|---|---|---|---|---|
| | | 30 | 60 | 120 | 180 | 240 |
| Compound XIV | | | | | | |
| M ± m | 3.72 ± 0.42 | 5.59 ± 1.12 | 4.7 ± 0.51 | 7.3 ± 1.09** | | 6.78 ± 0.504** |
| Latent time of NT (%) | 100 | 150.3 | 126.3 | 196.2 | | 182.3 |
| Analgesia (%) | | 50.3 | 26.3 | 96.2 | | 82.3 |
| Compound XXVI | | | | | | |
| M ± m | 5.7 ± 0.6 | 8.3 ± 0.9* | 10.2 ± 1.2* | 7.1 ± 0.4* | | |
| Latent time of NT (%) | 100 | 143.1 | 176.4 | 124.1 | | |
| Analgesia (%) | | 43.1 | 76.4 | 24.1 | | |
| Compound XXVII | | | | | | |
| M ± m | 5.3 ± 0.5 | 8.5 ± 0.9* | 10.7 ± 1.1** | 9.1 ± 1.3* | | |
| Latent time of NT (%) | 100 | 160.0 | 201.9 | 171.7 | | |
| Analgesia (%) | | 60.0 | 101.9 | 71.7 | | |
| Compound XXVIII | | | | | | |
| M ± m | 4.8 ± 0.7 | 9.2 ± 1.8* | 8.1 ± 1.0* | 11.6 ± 2.5* | | |
| Latent time of NT (%) | 100 | 191.7 | 168.8 | 241.7 | | |
| Analgesia (%) | | 91.7 | 68.8 | 141.7 | | |
| Compound XXIX | | | | | | |
| M ± m | 3.2 ± 0.2 | 6.3 ± 1.2* | 7.2 ± 0.8* | 8.0 ± 1.0* | | |
| Latent time of NT (%) | 100 | 196.9 | 225 | 250 | | |
| Analgesia (%) | | 196.9 | 125 | 150 | | |
| Compound XXX | | | | | | |
| M ± m | 4.1 ± 0.3 | 6.9 ± 0.8* | 9.0 ± 0.9** | 9.1 ± 1.4* | | |
| Latent time of NT (%) | 100 | 168.3 | 213.8 | 221.9 | | |
| Analgesia (%) | | 68.3 | 113.8 | 121.9 | | |
| Analgin, 150 mg/kg | | | | | | |
| M ± m | 4.85 ± 0.44 | 7.44 ± 1.22** | 7.29 ± 0.71* | 6.25 ± 0.75 | | 5.35 ± 0.38 |
| Latent time of NT (%) | 100 | 153.4 | 150.3 | 128.9 | | 110.3 |
| Analgesia (%) | | 53.4 | 50.3 | 28.9 | | 10.3 |
| Paracetamol, 200 mg/kg | | | | | | |
| M ± m | 3.95 ± 0.21 | 9.44 ± 1.3** | 6.24 ± 0.82** | 7.6 ± 1.15** | | |
| Latent time of NT (%) | 100 | 238.9 | 158 | 192.0 | | |
| Analgesia (%) | | 138.9 | 58.0 | 92.0 | | |

*P < 0.05;
**0.01 versus background parameters

The data obtained show that compounds of general formula I in the "hot plate" test demonstrate a significant activity considerably elevating nociception threshold. At the same time, analgetic effect comparable with that of the reference drugs is achieved in using doses 0.1 to 10 mg/kg, advantageously 1 to 10 mg/kg which are by one-two orders lower than the dose of the reference drug Paracetamol possessing analgetic and antipyretic action. The data presented in Table 7 also show that analgetic effect of compounds of general formula I averages from 50 to maximum 150% that may be considered as a prolonged one as it is preserved for a long time that in a number of cases is more than four hours.

Thus, compounds of general formula I by the degree of analgetic effect are comparable with the known non-narcotic analgetics (Analgin, Paracetamol), and by duration of analgetic effect, they exceed the reference drugs, their acting doses proving to be by an order lower than in the reference non-narcotic analgetics.

EXAMPLE 21

Study of the Effect of Compounds of General Formula I on Carrageenan Edema of Rat Paw The tests were conducted on males of outbreed white rats weighing 250-270 grams. The model of carrageenan edema was used which model is described in Winter et al. In: DeRosa M., Giroud J. P. Willoughby D. A. Studies of the mediators of acute inflammatory response induced in rats in different sites by carrageenan and turpentine.//J. Pharmacol. 1971. V. 104. P. 15-29.

0.1 ml 1% carrageenan solution (SERVA) was subplantarly injected into a right paw of rats. The animals were placed into individual chambers. 1% ointment was applied on the paw immediately following and at 1 and 2 hours post carrageenan administration. Paw volume was measured using a pletismometer (Ugo Besile) at 4 hours post carrageenan administration. Therapeutic effect of the ointment was assessed by the inhibition degree of inflammatory reaction as compared to an intact left paw of the given animal and to a paw reaction of a control (untreated) group of rats. Inhibition of inflammatory reaction expressed in percent was calculated according to the formula:

$$\text{Volume gain} = \frac{\text{Difference} \times 100}{\text{Left paw volume}}$$

$$\text{Edema inhibition} = 100 - \frac{\text{Volume gain}_{(test)} \times 100}{\text{Volume gain}_{(control)}}$$

The data obtained are presented in Table 8.

TABLE 8

The effect of compounds of general formula I (1% ointment) on the development of carrageenan edema of rat pa (M ± m)

| Number of rats n = 8 | Paw volume gain (%) | Edema inhibition (%) |
| --- | --- | --- |
| Control | 70.2 | — |
| Compound IX (1% ointment) | 32.9 | 53.1 |
| Indomethacin (10% ointment) | 45.0 | 50.0 |

The results presented in Table 8 demonstrate a pronounced anti-inflammatory activity of compounds of formula I comparable with activity of the reference drug from the NSAID group, indomethacin, effective dose of the compound being by one order lower than in the reference drug.

EXAMPLE 22

Study of Ulcerogenic Effect of Compound of General Formula I

The tests were carried out on females of outbreed rats weighing 300-320 grams. The compounds tested were administered once intragastrally at a dose 30 mg/kg to rats deprived of feed for 24 hours prior to the test. Animals in the control group were administered distilled water in the same volume. At 24 hours the animals were sacrificed and stomachs were extracted. An empty stomach was filled with 2% formalin solution and it was placed into a beaker with formalin. 30 minutes later, the stomach was opened along the great curvature, expanded on a slide, fixed and washed with distilled water. Using the magnifying glass MBS-9 (8-fold magnification) length and width of gastric mucosa defects was measured and area in mm$^2$ was calculated (1 division of the magnifying glass ruler=0.1 mm). Ulcerogenic effect of a substance was assessed by ulcerous lesion area of gastric mucosa according to the technique presented in Rukovodstvo po experimental'nomu (doklinicheskomu) izucheniju novykh pharmacologicheskikh veshchestv (the Guide on Experimental (pre-clinical) Study of Novel Pharmacological Substances)./Moscow. "Remedium" publishers. 2000, 398 pages.

The data obtained are presented in Table 9.

TABLE 9

A comparative study of the effect of compounds of general formula I and Indomethacin at a dose 30 mg/kg on gastric mucosa of rats (M ± m)

| Number of rats, n = 5 | Area of ulcerous lesion, mm$^2$ |
| --- | --- |
| Control | 0 |
| Compound IX | 0 |
| Indomethacin | 7.3 ± 1.75 |

The data obtained show that in intra-gastric administration of the compound of general formula I at a dose 30 mg/kg ulcerous lesion of gastric mucosa is absent.

EXAMPLE 23

Study of Spasmolitic Action of Compounds of General Formula I

The model of serotonin-induced soft muscular contracture of an uterine horn [Blattner H. G., Dehnert H. et al. Experiments on isolated smooth muscle preparation. Ed. J. M. Barnden and R. Colson, 1980] was created on females of Wistar rats weighing 300-350 grams. A prepared smooth muscle preparation (SMP) was placed into a thermo-regulated chamber (+37° C.) containing Tirode solution with lowered calcium content in order to prevent spontaneous contractive activity of the smooth muscle preparation. Contraction of the uterine horn was recorded using the mechanotron 6M×2B connected to the polygraph KPS-4; initial load to the object was 0.5-0.7 grams.

Contracture of the SMP was induced by introduction into incubation medium of 0.1 ml serotonin (Sigma) at concentration $10^{-5}$ M. 30-60 seconds post administration of the mediator, a peak contraction amplitude of the uterine horn was recorded. Compound IX was introduced into the chamber at the peak amplitude of contractions or under conditions of incubation (within the same range of concentrations) for 15 minutes.

The effect of compound IX being tested was assessed by a number of contractions and by lowering the amplitude value.

The results are presented in Table 10.

TABLE 10

The effect of compounds of general formula I on serotonin-induced contracture of rat uterine horn's SMP

| | Rate of contractions of the rat uterine horn's SMP during 5 minutes | Inhibition of contractions of the rat uterine horn's SMP, % |
| --- | --- | --- |
| Control (serotonin-induced contracture) | 9 | 0 |
| Compound IX at the peak serotonin-induced contracture | 5 | 44.4 |
| Pre-incubation of compound IX | 4 (with subsequent blockade) | 55.6 |

In adding compound IX at the peak serotonin-induced contracture of the uterine horn's SMP, slowing rate of contractions (during 5 minutes) of the rat uterine horn's smooth muscle preparation occurred from 9 contractions in the control down to 5 contractions in the test (see Table 10).

Under pre-incubation conditions of compound IX, slowing rate of contractions in response to serotonin was also observed (4 contractions during 5 minutes) with subsequent complete blockade of the SMP contracture (Table 10).

Thus, compound IX under in vitro conditions shows an spasmolitic action (at the peak serotonin-induced SMP contraction) and inhibits the development of SMP contracture in preventive administration.

EXAMPLE 24

Study of Anti-Hypoxic Action of Compounds of General Formula I

In order to imitate acute oxygen insufficiency the hypoxia model with hypercapnia in a hermetic volume was used (Luk'yanova L. D., Gatsura V. V., Pastushenkov L. V. Metodicheskiye recomendatsii po experimental'nomu izucheniju preparatov, predlagajemykh dlya klinicheskogo isuchenija v kachestve antihypoxicheskikh sredsyv (Methodological recommendations on experimental study of preparations proposed for clinical examination as anti-hypoxic agents). Moscow. 1960. P. 1-19]. Male rats weighing 27-29 grams were individually placed into 260 ml glass jars which were hermetically closed. As the animals consume oxygen, its concentration in the vessel lowers that results in death of the animals. Life span of the mice in minutes was recorded.

The data obtained are presented in Table 11.

TABLE 11

The effect of compounds of general formula I on life span of mice in the model of hypoxic hypoxia with hypercapnia

| Number of mice n = 10 | Duration of hypoxia, minutes | | |
|---|---|---|---|
| | Control | Compound IX 10 mg/kg | Compound IX 50 mg/kg |
| M ± m | 25.6 ± 0.6 | 25.3 ± 0.8 | 32.6 ± 2.6* |
| % change from the control | | 0 | +27 |

" - P < 0.05; statistically significant difference versus the control group

Compound IX at a dose 50 mg/kg significantly extends life span of mice under the condition of hypoxic hypoxia by 27.3%.

The experimental results suggest that compound IX shows anti-hypoxic action.

EXAMPLE 25

Study of Anti-Depressive Action of Compounds of General Formula I in the "Behavioral Despair" Test (Effect on Immobilization Duration)

The "behavioral despair" test according to Porsolt [R. D. Porsolt, A. Bertin and M. Jalfre.//in mice: A primary Screening Test for Antidepressants. Arch. Int. Pharmacodyn., 1977, 229, p. 327-336] is a predictive test for drugs with antidepressant action.

Stress state in mice (weighing 27-30 grams) is induced by forced swimming. Animals are placed into a cylinder (height 25 cm, diameter 10 cm) filled to ⅓ with water at temperature 21-23° C. The animals cannot escape from the cylinder by themselves. Following a short time of activity the animals develop a so called "behavioral depression" characterized by hovering of animals, immobilization duration of which can be fixed. The experiment is carried out in two days. One a first day, animals are placed into the cylinder for 15 minutes (pretest). After removal from water, the animals are dried and preparations under testing are administered. At 24 hours, the preparations are administered again and one hour later the animals are placed into the cylinder for 6 minutes. During first two minutes the animals are actively swimming; during the subsequent four minutes, behavioral depression develops manifested by immobilization (hovering) which is fixed for 4 minutes and is measure in seconds. Compound IX and the reference antidepressant drug Fluoxetin were administered orally at a dose 50 mg/kg.

The data obtained are presented in Table 12.

TABLE 12

The effect of compound IX and Fluoxetin on immobilization time in the "behavioral despair" test

| | Duration of hypoxia, minutes | | |
|---|---|---|---|
| | Control | Compound IX 50 mg/kg | Fluoxetin 50 mg/kg |
| M ± m | 195.0 ± 10.3 | 154.0 ± 11.7* | 131.0 ± 16.5** |
| % change from the control | | −21 | −33 |

" - P < 0.05,
**P < 0.01 - statistically significant difference versus the control group In the "behavioral despair" test, compound IX as well as the antidepressant Fluoxetin caused a statistically significant shortening immobilization time in mice.

Thus, in the action spectrum of compound IX, a pharmacological effect has been found (shortening immobilization time in the "behavioral despair" test according to Porsolt) characteristic of preparations belonging to the group of antidepressants.

EXAMPLES OF UNIT DOSAGE FORMS

EXAMPLE 26

A. Tablet Form

A tablet form is manufactured using the ingredients presented below:

| | |
|---|---|
| A compound corresponding to general formula (I) | 5-100 mg |
| Potato starch | 20-50 mg |
| Magnesium stearate | 3 mg |
| Aerosyl | 1 mg |
| Lactose | up to 300 mg |

The components are mixed and compressed to form tablets weighing 300 mg each.

B. Suppositoria

Example of a Suppositorium Composition

| | |
|---|---|
| A compound corresponding to general formula (I) | 5-100 mg |
| Cocoa butter | an amount needed to manufacture a suppositorium. |

If needed, manufacturing rectal, vaginal and urethral suppositoria is possible with respective excipients.

C. Ointments

Example of an Ointment Composition

| A compound corresponding to general formula (I) | 0.05-0.5 g |
|---|---|
| Petrolatum | 10 g |

Ointments are manufactured according to a generally known technology.

D. Gels

Example of a Gel Composition

| A compound corresponding to general formula (I) | 100 mg |
|---|---|
| Carbopol | 200 mg |
| Benzyl alcohol | 20 mg |
| Ethyl alcohol | 300 mg |
| Water | up to 10 g |

Thus, the present invention relates to novel compounds of general formula I, to simple and preparative methods for synthesis of novel and known compounds and to use thereof as non-steroid anti-inflammatory agents, cyclooxygenase inhibitors, possessing anti-inflammatory and advantageous analgetic action and showing no adverse ulcerogenic effect.

The results of the pharmacological studies suggest that the claimed compounds possess an unique capability to exert a therapeutic effect in exposure to the following extreme factors: emotional stress, pain syndrome, hypoxia, inflammation, spasms, as well as to cope disorders caused by Parkinson's disease, as well as to potentiate other analgetics.

The invention claimed is:

1. An agent possessing analgetic, anti-inflammatory, spasmolitic, anti-hypoxic, antidepressant and anti-Parkinsonistic properties as well as capability to potentiate effect of other analgetics comprising the compound of general formula I

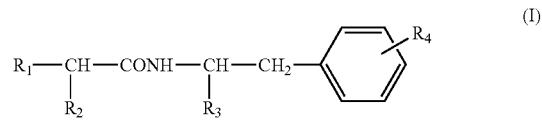

wherein $R_1$ is

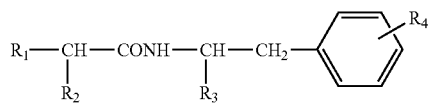

where $R_5$ is hydrogen or hydroxy group;

$R_2$ is hydrogen or amino group optionally substituted with $CH_3(CH_2)_mCO$—, where m is 0 to 4;

$R_3$ is hydrogen, —COOH, —COOR$_6$, where $R_6$ is $C_1$-$C_6$ alkyl or

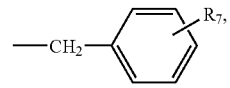

where $R_7$ is hydrogen or a hydroxy group, $R_4$ is hydrogen, a hydroxy group; or a pharmaceutically acceptable salt thereof.

2. A method for treating a patient in need of an agent possessing analgetic, anti-inflammatory, spasmolitic, anti-hypoxic, antidepressant or anti-Parkinsonistic activity or possessing capability to potentiate effect of other analgetics, the method comprising administering to the patient a compound of general formula I

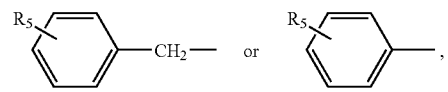

wherein $R_1$ is

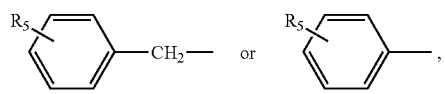

where $R_5$ is hydrogen or hydroxy group;

$R_2$ is hydrogen or amino group optionally substituted with $CH_3(CH_2)_mCO$—, where m is 0 to 4;

$R_3$ is hydrogen, —COOH, —COOR$_6$, where $R_6$ is $C_1$-$C_6$ alkyl or

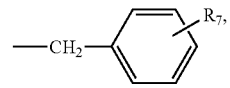

where $R_7$ is hydrogen or a hydroxy group, $R_4$ is hydrogen, a hydroxy group; or a pharmaceutically acceptable salt thereof.

3. A method for treating pain syndromes of different genesis, inflammatory and inflammatory-degenerative diseases of joints and connective tissue as well as skeletal-muscular system, other diseases accompanied by inflammation, spasms, depression, hypoxia as well as signs of Parkinsonism comprising administration to a mammal of an effective amount of the compound of general formula I

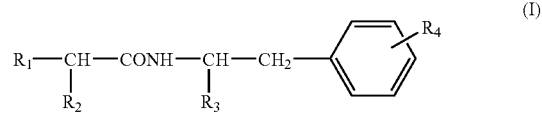

wherein $R_1$ is

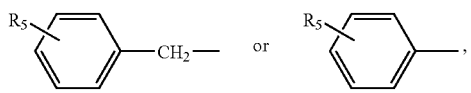

wherein $R_5$ is hydrogen or hydroxy group;
$R_2$ is hydrogen or amino group optionally substituted with $CH_3(CH_2)_mCO-$, where m is 0 to 4;
$R_3$ is hydrogen, —COOH, —COOR$_6$, where $R_6$ is $C_1$-$C_6$ alkyl or

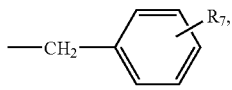

where $R_7$ is hydrogen or a hydroxy group,
$R_4$ is hydrogen, a hydroxy group; or a pharmaceutically acceptable salt thereof.

4. The method according to claim 3 of treating postoperative pain, posttraumatic pain as well as pain syndromes of gynecological, neurological, cancerous, dental origin, rheumatoid arthritis, arthropathy, Bekhterev's disease, non-specific spondylloarthritis, gout arthritis, osteoarthrosis, extra-articular rheumatic fever and thrombophlebitis, as well as emotional-stress states and disorders caused by spasms, hypoxia and accompanying Parkinson's disease.

5. The method according to claim 3 or 4 wherein a compound of general formula (I) is administered in a combination with other analgetics.

6. The agent of claim 1, wherein, in the compound of general formula I or the pharmaceutically acceptable salt thereof,
$R_3$ is hydrogen, —COOH, —COOR$_6$, where $R_6$ is $CH_3$ or

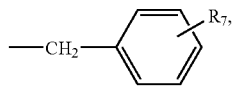

where $R_7$ is hydrogen or a hydroxy group, $R_4$ is hydrogen, a hydroxy group.

7. The agent of claim 1, wherein, in the compound of general formula I, $R_3$ is —COOH or —COOCH$_3$.

8. The agent of claim 1, wherein the compound of general formula I is selected from
p-hydroxyphenylacetyltyrosine,
p-hydroxyphenylacetylphenylalanine,
p-hydroxyphenylacetyltyrosine methyl ester,
p-hydroxyphenylacetylphenylalanine methyl ester,
p-hydroxyphenylacetyltyrosine benzyl ester,
p-hydroxyphenylacetylphenylalanine benzyl ester,
N-acetyltyrosylphenylethylamine,
N-acetyltyrosyltyramine,
p-hydroxyphenylacetyltyramine,
p-hydroxyphenylacetylphenylethylamine,
3-(p-hydroxyphenyl)propionylphenylalanine benzyl ester,
3-phenylpropionylphenylalanine benzyl ester,
or pharmaceutically acceptable salts thereof.

* * * * *